United States Patent [19]

Schallner et al.

[11] Patent Number: 4,614,533

[45] Date of Patent: Sep. 30, 1986

[54] HERBICIDAL 5-AMINO-1-PHENYLPYRAZOLES

[75] Inventors: Otto Schallner, Monheim; Reinhold Gehring, Wuppertal; Erich Klauke, Odenthal; Jörg Stetter, Wuppertal; Heinz-Jürgen Wroblowsky, Langenfeld; Robert R. Schmidt, Bergisch-Gladbach; Hans-Joachim Santel, Cologne, all of Fed. Rep. of Germany

[73] Assignee: Bayer Aktiengesellschaft, Leverkusen, Fed. Rep. of Germany

[21] Appl. No.: 690,347

[22] Filed: Jan. 10, 1985

[30] Foreign Application Priority Data

Jan. 24, 1984 [DE] Fed. Rep. of Germany ....... 3402308

[51] Int. Cl.⁴ ...................... A01N 43/56; A01N 57/16
[52] U.S. Cl. .............................. 71/92; 71/86; 71/87; 548/111; 548/362; 548/375; 548/376; 548/377
[58] Field of Search ............................... 71/92, 86, 87

[56] References Cited

FOREIGN PATENT DOCUMENTS 226388  1/1959  Australia .............................. 548/362
0053699 6/1982  European Pat. Off. ............ 564/307
202612  9/1983  German Democratic Rep. .... 71/92

OTHER PUBLICATIONS

Journal of Organic Chemistry, vol. 36, Sep.–Dec. 1971, pp. 2972–2974, Y, Ahmad and P. A. S. Smith, "Pyrazolotriazines . . . with Amino Groups".
Journal of Heterocyclic Chemistry, vol. 7, No. 1, Feb. 1970, pp. 345–349, M. D. Coburn, "Picrylamino-substituted Heterocycles . . . (1,2)".
Chemical Abstracts, vol. 62, May 24–Jun. 21, 1965, Col. 13137, A. Takamizawa et al, "Synthesis of pyrazol derivatives . . . with aryl-hydrazines".

Primary Examiner—Richard A. Schwartz
Assistant Examiner—Kurt G. Briscoe
Attorney, Agent, or Firm—Sprung Horn Kramer & Woods

[57] ABSTRACT

Herbicidally active 5-amino-1-phenyl-pyrazoles, most of which are new, of the formula

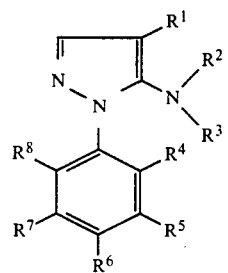

7 Claims, No Drawings

HERBICIDAL 5-AMINO-1-PHENYLPYRAZOLES

The present invention relates to the use of 5-amino-1-phenyl-pyrazoles, some of which are known, as herbicides.

It is known that certain 5-amino-1-phenyl-pyrazoles which are substituted in the 4-position by a cyano group, such as, for example, 4-cyano-5-propionylamino-1-(2,4,6-trichlorophenyl)-pyrazole, possess herbicidal properties (see, for example, European Pat. No. 34,945).

However, their herbicidal activity against some problem weeds, like their compatibility with important crop plants, is not always completely satisfactory in all fields of use.

5-Amino-1-phenylpyrazoles which are unsubstituted in the 4-position or substituted in the 4-position by methyl or phenyl, such as, for example 5-amino-1-(2,4-dinitrophenyl)-4-methylpyrazole, 5-amino-1-(2,4-dinitrophenyl)-4-phenylpyrazole, 5-amino-4-(4-chlorophenyl)-1-(2,4-dinitrophenyl)-pyrazole, 5-amino-1-(2,4-dinitrophenyl)-4-(4-methoxyphenyl)-pyrazole or 5-acetamido-1-(2,4,6-trinitrophenyl)-pyrazole, are also known (see J. Org. Chemistry 36, 2972–2974 [1971]; J. Heterocycl. Chem. 7, 345–349 [1970] and C.A. 62, 13137c). However, nothing is known about their activity as herbicides.

It has been found that the substituted 5-amino-1-phenyl-pyrazoles, some of which are known, of the general formula (I)

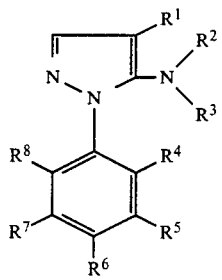

in which $R^1$ represents hydrogen, nitrose, nitro, halogen, alkyl, halogenoalkyl, optionally substituted aryl or one of the radicals —S(O)$_n$—R$^9$;

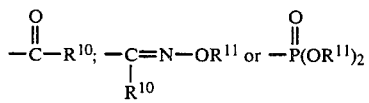

$R^2$ represents hydrogen or a radical

$R^3$ independently of $R^2$ represents the same radicals as $R^2$ and additionally represents alkyl, $R^4$ and $R^6$ independently of one another represent cyano, nitro, halogen, alkyl, alkoxy, alkoxy carbonyl, halogenoalkyl, halogenoalkoxy or a radical —S(O)$_n$—R$^{13}$, and $R^5$, $R^7$ and $R^8$ independently of one another and of $R^4$ and $R^6$ represent the same radicals as $R^4$ and $R^6$ and additionally represent hydrogen, and $R^9$ represents hydrogen, hydroxyl, halogen, amino, alkylamino, dialkylamino, alkyl, halogenoalkyl or optionally substituted aryl, $R^{10}$ represents hydrogen, alkyl or optionally substituted aryl, $R^{11}$ represents hydrogen, alkyl, halogenoalkyl, alkenyl, alkinyl or aralkyl, $R^{12}$ represents hydrogen, alkyl, alkenyl, alkinyl, halogenoalkyl, alkoxyalkyl, alkylthioalkyl, optionally substituted cycloalkyl, optionally substituted aryl, alkoxy, alkylthio, optionally substituted aryloxy, optionally substituted arylthio, alkylamino, dialkylamino or optionally substituted arylamino, $R^{13}$ represents alkyl, halogenoalkyl, amino, alkylamino or dialkylamino, X represents oxygen or sulphur, and n represents the numbers 0, 1 or 2, possess herbicidal properties, in particular selective herbicidal properties.

Surprisingly, the substituted 5-amino-1-phenyl-pyrazoles of the formula (I) which are to be used according to the invention exhibit, in addition to an improved herbicidal action against certain weeds, substantially improved compatibility with important crop plants compared with the 4-cyano-5-amino-1-phenyl-pyrazoles known from the prior art, such as, for example, 4-cyano-5-propionylamino-1-(2,4,6-trichlorophenyl)-pyrazole, which is a similar compound chemically and in terms of its action.

The substituted 5-amino-1-phenyl-pyrazoles to be used according to the invention thus represent an enrichment of the art.

Formula (I) gives a general definition of the substituted 5-amino-1-phenyl-pyrazoles to be used according to the invention. Preferred compounds of the formula (I) are those in which $R^1$ represents hydrogen, nitroso, nitro, halogen, alkyl or halogenoalkyl, each of which is straight-chain or branched and each of which has up to 6 carbon atoms and, in the case of halogenoalkyl, up to 9 identical or different halogen atoms, or represents phenyl which is optionally monosubstituted or polysubstituted by identical or different substituents from amongst halogen, nitro, alkyl, alkoxy or halogenoalkyl, each having up to 4 carbon atoms, or represents one of the radicals —S(O)$_n$—R$^9$;

$R^2$ represents hydrogen or a radical

$R^3$ independently of $R^2$ represents the same radicals as $R^2$, and additionally represents straight-chain or branched alkyl having up to 4 carbon atoms, $R^4$ and $R^6$ independently of one another represent cyano, nitro, halogen, or alkyl, alkoxy or alkoxycarbonyl, each of which is straight-chain or branched and each of which has up to 4 carbon atoms, and furthermore represents halogenoalkyl or halogenoalkoxy, each of which is straight-chain or branched and each of which has up to 4 carbon atoms and up to 9 identical or different halogen atoms, or represents a radical —S(O)$_n$—R$^{13}$, and R$^5$, R$^7$ and R$^8$ independently of one another and of R$^4$ and R$^6$ represent the same radicals as R$^4$ and R$^6$ and additionally represent hydrogen and R$^9$ represents hydrogen, hydroxyl, fluorine, chlorine, bromine, amino or alkylamino, dialkylamino, alkyl or halogenoalkyl, each of which is straight-chain or branched and each of which has up to 4 carbon atoms in the individual alkyl parts, and, in the case of halogenoalkyl, up to 9 identical or different halogen atoms, and represents phenyl which is optionally monosubstituted or polysubstituted by identical or different substituents, the following being suitable substituents: halogen, alkyl, alkoxy or halogenoalkyl, each of which is straight-chain or branched and each of which has up to 4 carbon atoms and, in the case of halogenoalkyl, up to 9 identical or different halogen atoms, R$^{10}$ represents hydrogen, straight-chain or branched alkyl having up to 4 carbon atoms, or phenyl which is optionally monosubstituted or polysubstituted by identical or different substituents, suitable phenyl substituents being those mentioned in the case of R$^9$, R$^{11}$ represents hydrogen, halogenoalkyl having up to 4 carbon atoms and up to 6 identical or different halogen atoms, alkyl, alkenyl or alkinyl, each of which is straight-chain or branched and each of which has up to 8 carbon atoms, and straight-chain or branched phenylalkyl having up to 4 carbon atoms in the alkyl part, R$^{12}$ represents hydrogen, or alkyl which is straight-chain or branched and which has 1 to 12 carbon atoms, or alkenyl, alkinyl, alkoxyalkyl, alkylthioalkyl, alkoxy, alkylthio, alkylamino, dialkylamino or halogenoalkyl, each of which is straight-chain or branched and each of which has up to 4 carbon atoms in the individual alkyl parts and, in the case of halogenoalkyl, up to 9 identical or different halogen atoms, and furthermore represents cycloalkyl which has 3 to 7 carbon atoms and is optionally monosubstituted or polysubstituted by identical or different substituents from amongst halogen, lower alkyl or lower halogenoalkyl, and represents phenyl, phenoxy, phenylthio or phenylamino, each of which is optionally monosubstituted or polysubstituted by identical or different substituents, suitable phenyl substituents being those stated in the case of R$^9$;

R$^{13}$ represents amino, and alkyl, alkylamino, dialkylamino or halogenoalkyl, each of which is straight-chain or branched and each of which has up to 4 carbon atoms in the individual alkyl parts and, in the case of halogenoalkyl, up to 9 identical or different halogen atoms, X represents oxygen or sulphur and n represents the number 0, 1 or 2.

Particularly preferred compounds of the formula (I) are those in which:

R$^1$ represents hydrogen, nitroso, nitro, fluorine, chlorine, bromine, methyl, ethyl, n- and i-propyl, n-, i, s- and t-butyl, trifluoromethyl, or phenyl which is optionally monosubstituted to trisubstituted by identical or different substituents from amongst fluorine, chlorine, bromine, nitro, methyl, ethyl, methoxy and trifluoromethyl, or represents one of the radicals —S(O)$_n$—R$^9$;

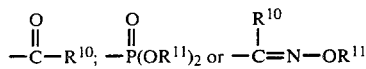

R$^2$ represents hydrogen or a radical

R$^3$ independently of R$^2$ represents the same radicals as R$^2$ and additionally represents methyl, ethyl, n- and i-propyl, n-, i-, s- and t-butyl, R$^4$ and R$^6$ independently of one another represent cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical —S(O)$_n$—R$^{12}$, and R$^5$, R$^7$ and R$^8$ independently of one another and of R$^4$ and R$^6$ represent the same radicals as R$^4$ and R$^6$ and additionally represent hydrogen, and R$^2$ represents hydrogen, hydroxyl, fluorine, chlorine, bromine, amino, methylamino, dimethylamino, ethylamino, diethylamino diisopropylamino, di-n-butylamino, methyl, ethyl, dichlorofluoromethyl or trifluoromethyl, and represents phenyl which is optionally mono-substituted to trisubstituted by identical or different substituents from amongst methyl, methoxy, trifluoromethyl and chlorine, R$^{10}$ represents hydrogen, methyl, ethyl, n- and i-propyl, and represents phenyl which is optionally monosubstituted to trisubstituted by identical or different substituents from amongst methyl, methoxy, trifluoromethyl and chlorine, R$^{11}$ represents hydrogen, methyl, ethyl, n- and i-propyl, n-, i-, s- and t-butyl, allyl, butenyl, propargyl, benzyl, chloroethyl or bromoethyl, R$^{12}$ represents hydrogen, methyl, ethyl, n- and i-propyl, undecyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, chloropropyl or heptafluoro-n-propyl, or represents cyclopentyl, cyclohexyl or cyclopropyl which is optionally monosubstituted to tetrasubstituted by identical or different substituents from amongst fluorine, chlorine, bromine, methyl and trifluoromethyl, and represents phenyl, phenoxy, phenylthio or phenylamino, each of which is optionally monosubstituted to trisubstituted by identical or different substituents from amongst methyl, methoxy, chlorine and trifluoromethyl, $R^{13}$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, X represents oxygen or sulphur, and n represents the number 0, 1 or 2.

In addition to the compounds mentioned in the preparation examples, the following 5-amino-1-phenyl-pyrazoles of the general formula (I) may be mentioned individually:

TABLE 1

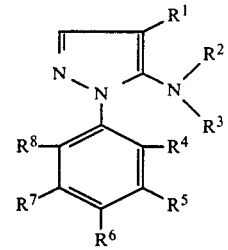

(I)

| $R^1$ | $R^2$ | $R^3$ | $R^4$ | $R^5$ | $R^6$ | $R^7$ | $R^8$ |
|---|---|---|---|---|---|---|---|
| H | CH$_3$CO | H | Cl | H | Cl | H | H |
| H | CH$_3$CO | CH$_3$CO | Cl | H | Cl | H | H |
| H | CH$_3$CO | H | Cl | H | Cl | H | Cl |
| H | CH$_3$CO | CH$_3$ | Cl | H | Cl | H | Cl |
| H | CH$_3$CO | H | NO$_2$ | H | NO$_2$ | H | H |
| H | H | H | Cl | H | CF$_3$ | H | Cl |
| H | CH$_3$CO | H | Cl | H | OCF$_3$ | H | H |
| H | C$_2$H$_5$CO | H | CF$_3$ | H | SCF$_3$ | H | H |
| H | C$_2$H$_5$CO | H | Cl | Cl | Cl | H | H |
| H | H | H | Cl | Cl | Cl | H | H |
| H | CH$_3$CO | CH$_3$CO | Cl | Cl | Cl | H | H |
| H | CH$_3$CO | C$_2$H$_5$CO | Cl | Cl | Cl | H | H |
| H | C$_2$H$_5$CO | H | Cl | H | CF$_3$ | H | Cl |
| H | CH$_3$CO | H | Cl | H | CF$_3$ | H | Cl |
| H | ▷⟨CO/H | H | Cl | H | CF$_3$ | H | Cl |
| H | CH$_3$OCO | H | Cl | H | CF$_3$ | H | Cl |
| H | n-C$_3$H$_7$CO | H | Cl | H | CF$_3$ | H | Cl |
| H | CH$_3$CO | CH$_3$CO | Cl | H | CF$_3$ | H | Cl |
| H | C$_2$H$_5$CO | H | Cl | H | OCF$_3$ | H | H |
| H | ▷⟨CO/H | H | Cl | H | OCF$_3$ | H | H |
| H | n-C$_4$H$_9$—CO | H | Cl | H | OCF$_3$ | H | H |
| H | C$_2$H$_5$CO | H | Cl | H | SCF$_3$ | H | Cl |
| H | n-C$_3$H$_7$CO | H | Cl | H | SCF$_3$ | H | Cl |
| H | ▷⟨CO/H | H | Cl | H | SCF$_3$ | H | Cl |
| H | CH$_3$CO | H | Cl | H | SCF$_3$ | H | Cl |
| H | CH$_3$OCO | H | Cl | H | SCF$_3$ | H | Cl |
| H | CH$_3$OCO | H | Cl | H | OCF$_3$ | H | H |
| H | C$_2$H$_5$CO | H | Cl | Cl | Cl | H | Cl |
| H | CH$_3$CO | H | Cl | Cl | Cl | H | Cl |
| H | CH$_3$CO | H | Cl | Cl | Cl | H | H |
| H | ▷⟨CO/H | H | Cl | Cl | Cl | H | Cl |
| H | CH$_3$OCO | H | Cl | Cl | Cl | H | Cl |
| H | CH$_3$CO | H | Cl | Cl | CF$_3$ | H | Cl |
| H | C$_2$H$_5$CO | H | Cl | Cl | CF$_3$ | H | Cl |
| H | n-C$_3$H$_7$CO | H | Cl | Cl | CF$_3$ | H | Cl |
| H | ▷⟨CO/H | H | Cl | Cl | CF$_3$ | H | Cl |
| H | CH$_3$OCO | H | Cl | Cl | CF$_3$ | H | Cl |

TABLE 1-continued (I)

[Structure: pyrazole ring with R¹ at 4-position, N(R²)(R³) at 5-position, and N1 attached to phenyl ring bearing R⁴ (ortho), R⁵ (meta), R⁶ (para), R⁷ (meta), R⁸ (ortho)]

| R¹ | R² | R³ | R⁴ | R⁵ | R⁶ | R⁷ | R⁸ |
|---|---|---|---|---|---|---|---|
| H | —CO—NHCH₃ | H | Cl | Cl | Cl | H | H |
| H | —CO—NHCH₃ | H | Cl | H | CF₃ | H | Cl |
| H | CH₃CO | H | Cl | Cl | SCF₃ | H | H |
| H | CH₃CO | H | F | F | OCF₃ | H | F |
| H | C₂H₅CO | CH₃CO | F | F | OCF₃ | F | F |
| Cl | H | H | Cl | Cl | Cl | H | H |
| Cl | H | H | Cl | H | Cl | H | H |
| Cl | H | H | Cl | H | CF₃ | H | Cl |
| Cl | H | H | Cl | H | SCF₃ | H | Cl |
| Cl | CH₃CO | H | Cl | Cl | Cl | H | H |
| Cl | CH₃CO | H | Cl | Cl | OCF₃ | H | H |
| Cl | CH₃CO | CH₃ | Cl | Cl | SCF₃ | H | H |
| Cl | C₂H₅CO | H | F | F | OCF₃ | F | F |
| Cl | C₂H₅CO | H | Br | H | SCF₃ | H | H |
| Cl | C₂H₅CO | H | Cl | H | SCF₃ | H | Cl |
| Cl | C₂H₅CO | CH₃CO | Cl | Cl | SCF₃ | H | H |
| Cl | CH₃CO | CH₃CO | Cl | Cl | Cl | H | H |
| Cl | CH₃CO | C₂H₅CO | Cl | Cl | Cl | H | H |
| Cl | —CO—NHCH₃ | H | Cl | Cl | OCF₃ | H | H |
| Cl | —CO—OC₂H₅ | H | Br | H | OCF₃ | H | Br |
| Cl | —CO—C₆H₅ | H | NO₂ | H | NO₂ | H | NO₂ |
| Cl | —CO—CF₃ | H | NO₂ | H | NO₂ | H | H |
| Br | CH₃CO | H | Cl | Cl | Cl | H | H |
| Br | CH₃OCH₂CO | H | Cl | H | Cl | H | Cl |
| Br | CH₃SCF₂—CO | H | NO₂ | H | NO₂ | H | H |
| Br | CH₃CO | CH₃CO | Cl | Cl | CF₃ | H | H |
| Br | C₂H₅CO | CH₃CO | Cl | H | CF₃ | H | Cl |
| Br | CH₃CO | H | Cl | H | OCF₃ | H | Cl |
| Br | (CH₃)₂-cyclopropyl-CO— | H | F | H | OCF₃ | H | F |
| Br | cyclopropyl-CO— | H | F | F | OCF₃ | H | F |
| Br | (Cl,Cl)-cyclopropyl-CO— | H | F | F | SCF₃ | H | F |
| Br | H | H | F | H | SCF₃ | H | F |
| Br | C₂H₅CO | H | Cl | H | Cl | H | Cl |
| Br | 4-Cl-C₆H₄-CO— | H | Cl | H | Cl | H | H |
| Br | 4-CH₃O-C₆H₄-CO— | H | Cl | Cl | Cl | H | H |
| Br | CH₃CO | CH₃ | Cl | H | SO₂CF₃ | H | Cl |
| Br | F₃CCO | H | Cl | H | SOCF₃ | H | Cl |
| Br | ClCH₂CO | H | CF₃ | H | CF₃ | H | CF₃ |
| Br | Cl₂CHCO | H | CF₃ | H | SO₂CF₃ | H | CF₃ |
| I | H | H | Cl | Cl | Cl | H | H |
| I | H | H | Cl | H | Cl | H | Cl |
| I | H | H | Cl | H | CF₃ | H | Cl |
| I | CH₃CO | H | Cl | Cl | Cl | H | H |
| I | CH₃CO | H | Cl | H | CF₃ | H | Cl |

TABLE 1-continued $$\text{(I)}$$

Structure: Pyrazole with $R^1$ at 4-position, $NR^2R^3$ at 5-position, N1 attached to phenyl bearing $R^4$ (ortho), $R^5$ (meta), $R^6$ (para), $R^7$ (meta), $R^8$ (ortho).

| $R^1$ | $R^2$ | $R^3$ | $R^4$ | $R^5$ | $R^6$ | $R^7$ | $R^8$ |
|---|---|---|---|---|---|---|---|
| I | CH$_3$CO | CH$_3$CO | Cl | H | OCF$_3$ | H | Cl |
| I | CH$_3$CO | CH$_3$CO | CF$_3$ | H | SCF$_3$ | H | CF$_3$ |
| I | C$_2$H$_5$CO | H | CF$_3$ | H | SCF$_3$ | H | H |
| I | C$_2$H$_5$CO | CH$_3$CO | Br | H | CF$_3$ | H | Br |
| I | C$_2$H$_5$CO | CH$_3$ | Cl | Cl | Cl | H | H |
| I | C$_6$H$_5$CO | H | F | F | OCF$_3$ | F | F |
| I | 4-Cl-C$_6$H$_4$-CO— | H | Cl | H | OCF$_3$ | H | Cl |
| I | F$_3$C—CO | H | F | H | OCF$_3$ | H | F |
| I | ClCH$_2$CO | H | Cl | H | SCF$_3$ | H | Cl |
| I | Cl$_2$CH—CO | H | Cl | H | SO$_2$CF$_3$ | H | Cl |
| I | CH$_3$—CHCl—CO | H | F | F | SO$_2$CF$_3$ | F | F |
| I | cyclopropyl-CO— | H | Cl | Cl | Cl | H | H |
| CF$_3$ | H | H | Cl | H | Cl | H | Cl |
| CF$_3$ | H | H | NO$_2$ | H | NO$_2$ | H | NO$_2$ |
| CF$_3$ | CH$_3$CO | H | Cl | H | CF$_3$ | H | Cl |
| CF$_3$ | CH$_3$CO | H | Cl | H | OCF$_3$ | H | Cl |
| CF$_3$ | CH$_3$CO | CH$_3$ | Cl | Cl | CF$_3$ | H | H |
| CF$_3$ | CH$_3$CO | CH$_3$CO | Cl | Cl | Cl | H | H |
| CF$_3$ | C$_2$H$_5$CO | H | Cl | H | SCF$_3$ | H | Cl |
| CF$_3$ | C$_2$H$_5$CO | H | F | F | SCF$_3$ | H | F |
| CF$_3$ | C$_2$H$_5$CO | CH$_3$CO | F | F | OCF$_3$ | F | F |
| CF$_3$ | H$_6$C$_5$CO | H | Cl | Cl | SCF$_3$ | Cl | Cl |
| CF$_3$ | CH$_3$NHCO | H | Cl | H | SO$_2$CH$_3$ | H | Cl |
| CF$_3$ | 4-Cl-C$_6$H$_4$-CO— | H | Cl | H | SO$_2$CF$_3$ | H | Cl |
| CF$_3$ | 4-CH$_3$O-C$_6$H$_4$-CO— | H | Cl | Cl | Cl | H | H |
| CF$_3$ | 4-Cl-2-Cl-C$_6$H$_3$-CO— | H | Cl | H | Cl | H | Cl |
| CF$_3$ | cyclopropyl-CO— | H | Cl | Cl | Cl | H | H |
| CF$_3$ | C$_6$H$_5$OCO | H | CF$_3$ | H | CF$_3$ | H | H |
| CF$_3$ | C$_2$H$_5$OCO | H | Cl | H | CF$_3$ | H | Cl |
| NO$_2$ | H | H | Cl | Cl | Cl | H | H |
| NO$_2$ | H | H | Cl | F | Cl | H | Cl |
| NO$_2$ | H | H | Cl | H | CF$_3$ | H | Cl |

TABLE 1-continued (I)

| R¹ | R² | R³ | R⁴ | R⁵ | R⁶ | R⁷ | R⁸ |
|---|---|---|---|---|---|---|---|
| NO₂ | H | H | Cl | H | OCF₃ | H | Cl |
| NO₂ | H | H | Cl | H | SCF₃ | H | Cl |
| NO₂ | CH₃CO | H | Cl | Cl | Cl | H | H |
| NO₂ | CH₂CO | H | Cl | H | CF₃ | H | Cl |
| NO₂ | CH₃CO | H | CF₃ | H | CF₃ | H | CF₃ |
| NO₂ | CH₃CO | CH₃CO | CF₃ | H | CF₃ | H | H |
| NO₂ | CH₃CO | CH₃CO | Cl | Cl | Cl | H | H |
| NO₂ | CH₃CO | CH₃ | Cl | H | Cl | H | Cl |
| NO₂ | CH₃CO | CH₃ | CF₃ | H | CF₃ | H | H |
| NO₂ | C₂H₅CO | H | Cl | H | Cl | H | Cl |
| NO₂ | C₂H₅CO | CH₃CO | Cl | Cl | Cl | H | H |
| NO₂ | C₃H₅CO | H | F | F | F | F | F |
| NO₂ | C₂H₅CO | H | F | F | CF₃ | F | F |
| NO₂ | C₂H₅CO | H | Cl | Cl | Cl | H | H |
| NO₂ | C₆H₅CO | H | Cl | H | Cl | H | H |
| NO₂ | CH₃NHCO | H | Cl | Cl | Cl | H | H |
| NO₂ | CH₃NHCO | CH₃ | Cl | H | Cl | H | Cl |
| NO₂ | C₆H₅CO | H | Cl | Cl | Cl | Cl | Cl |
| NO₂ | 4-Cl-C₆H₄-CO | H | F | F | F | F | F |
| NO₂ | 4-Cl-C₆H₄-CO | H | F | H | CF₃ | H | F |
| NO₂ | 4-CH₃O-C₆H₄-CO | H | Cl | H | CF₃ | H | Cl |
| NO₂ | C₂H₅O—CO | H | Cl | Cl | CF₃ | H | H |
| NO₂ | C₂H₅O—CO | H | Cl | H | OCF₃ | H | Cl |
| NO₂ | C₆H₅O—CO | H | Cl | H | OCF₃ | H | H |
| NO₂ | C₆H₅O—CO | H | Cl | Cl | Cl | H | H |
| NO₂ | cyclopropyl-CO | H | Cl | H | SO₂CH₃ | H | Cl |
| NO₂ | cyclopropyl-CO | H | Cl | H | SO₂CF₃ | H | Cl |
| NO₂ | CH₃OCH₂CO | H | Cl | Cl | Cl | H | H |
| NO₂ | ClCH₂CO— | H | Cl | H | Cl | H | H |
| NO₂ | Cl₂CHCO | H | Cl | H | Cl | H | Cl |
| NO₂ | Cl₂CHCO | H | Cl | H | CF₃ | H | Cl |
| NO | H | H | Cl | Cl | Cl | H | H |
| NO | H | H | Cl | H | Cl | H | Cl |
| NO | H | H | Cl | H | CF₃ | H | Cl |
| NO | CH₃CO | H | Cl | Cl | Cl | H | H |
| NO | CH₃CO | H | Cl | H | Cl | H | Cl |
| NO | CH₃CO | H | Cl | H | CF₃ | H | Cl |
| NO | CH₃CO | CH₃CO | Cl | H | OCF₃ | H | Cl |
| NO | CH₃CO | CH₃ | Cl | Cl | CF₃ | Cl | Cl |
| NO | CH₃CO | C₂H₅CO | F | H | OCF₃ | H | F |
| NO | C₂H₅CO | H | F | F | OCF₃ | F | F |
| NO | C₂H₅CO | H | F | F | F | F | F |
| NO | ClCH₂CO | H | Cl | H | SO₂CH₃ | H | Cl |

TABLE 1-continued

(I)

| R¹ | R² | R³ | R⁴ | R⁵ | R⁶ | R⁷ | R⁸ |
|---|---|---|---|---|---|---|---|
| NO | Cl₂CHCO | H | Cl | H | SO₂CF₃ | H | Cl |
| NO | CF₃CO | H | Cl | Cl | SO₂CF₃ | H | H |
| NO | CH₃NHCO | H | Cl | H | Cl | H | H |
| NO | C₂H₅OCO | H | Cl | Cl | Cl | H | H |
| NO | CF₃CO | H | Cl | Cl | Cl | H | H |
| NO | C₆H₅CO | H | Cl | Cl | Cl | H | H |
| H—CO— | H | H | Cl | H | Cl | H | H |
| H—CO— | H | H | Cl | H | Cl | H | Cl |
| H—CO— | H | H | Cl | H | CF₃ | H | Cl |
| H—CO— | CH₃CO | H | Cl | H | CF₃ | H | Cl |
| H—CO— | CH₃CO | H | Cl | H | OCF₃ | H | Cl |
| H—CO— | CH₃CO | H | Cl | H | SCF₃ | H | Cl |
| H—CO— | CH₃CO | CH₃ | Cl | Cl | Cl | H | Cl |
| H—CO— | CH₃CO | CH₃ | Cl | H | CF₃ | H | Cl |
| H—CO— | C₂H₅CO | H | Cl | Cl | Cl | H | H |
| H—CO— | C₂H₅CO | H | Cl | H | Cl | H | Cl |
| H—CO— | C₂H₅CO | CH₃CO | Cl | Cl | Cl | H | Cl |
| H—CO— | CH₃CO | CH₃CO | Cl | H | CF₃ | H | Cl |
| H—CO— | C₂H₅O—CO | H | Cl | H | CF₃ | H | H |
| H—CO— | C₂H₅OCO | H | F | H | CF₃ | H | F |
| H—CO— |  | H | Cl | Cl | Cl | H | H |
| H—CO— | C₆H₅CO | H | Cl | H | Cl | H | Cl |
| H—CO— | C₆H₅OCO | H | F | F | F | F | F |
| CH₃—CO | H | H | NO₂ | H | NO₂ | H | H |
| CH₃—CO | H | H | NO₂ | H | CF₃ | H | H |
| CH₃—CO | CH₃CO | H | Cl | Cl | Cl | H | H |
| CH₃—CO | CH₃CO | H | Cl | H | Cl | H | Cl |
| CH₃—CO | CH₃CO | CH₃CO | Cl | H | Cl | H | H |
| CH₃—CO | C₂H₅CO | H | Cl | H | CF₃ | H | H |
| CH₃—CO | C₂H₅CO | H | Cl | H | CF₃ | H | Cl |
| CH₃—CO | C₂H₅CO | H | Cl | Cl | Cl | H | H |
| CH₃—CO— | CF₃CO | H | Cl | H | Cl | H | Cl |
| CH₃—CO— | CF₃CO | H | Cl | H | CF₃ | H | H |
| CH₃—CO— | ClCH₂CO | H | Cl | H | OCF₃ | H | Cl |
| CH₃—CO— | CH₃OCH₂CO | H | Cl | H | OCF₃ | H | Cl |
| CH₃—CO— | CH₃SCH₂CO | H | Cl | H | SCF₃ | H | Cl |
| CH₃—CO— | Cl₂CHCO | H | F | H | SCF₃ | H | F |
| CH₃—CO— | Cl₂CHCO | H | F | H | SO₂CF₃ | H | F |
| CH₃—CO— | CH₃—CHCO<br>\|<br>Cl | H | F | H | SO₂CF₃ | H | F |
| CH₃—CO— | Br—CH₂CO | H | F | F | F | F | F |
| HO—N=CH— | H | H | Cl | H | Cl | H | H |
| HO—N=CH— | H | H | Cl | H | CF₃ | H | H |
| HO—N=CH— | H | H | Cl | Cl | Cl | H | H |
| HO—N=CH— | H | H | F | F | F | F | F |
| HO—N=CH— | CH₃CO | H | Cl | Cl | Cl | H | H |
| HO—N=CH— | CH₃CO | H | Cl | H | Cl | H | Cl |
| HO—N=CH— | C₂H₅CO | H | Cl | H | CF₃ | H | Cl |
| HO—N=CH— | C₂H₅CO | H | Cl | H | Cl | H | H |
| HO—N=CH— | C₂H₅CO | C₂H₅CO | Cl | H | OCF₃ | H | Cl |
| HO—N=CH— | CH₃CO | CH₃CO | Cl | H | OCF₃ | H | Cl |
| HO—N=CH— | CF₃CO | CF₃CO | Cl | H | SCF₃ | H | Cl |
| HO—N=CH— | CF₃CO | H | Cl | H | OCH₃ | H | Cl |
| HO—N=CH— | ClCH₂CO | H | Cl | H | SCH₃ | H | Cl |
| HO—N=CH— | Cl₂CHCO | H | Cl | H | SO₂CH₃ | H | Cl |
| HO—N=CH— | CH₃OCH₂CO | H | Cl | H | SO₂CH₃ | H | Cl |
| HO—N=CH— | CH₃OCH₂CO | H | Cl | H | SO₂CF₃ | H | Cl |
| HO—N=CH— | CH₃SCH₂CO | H | Cl | Cl | Cl | H | H |
| CH₃O—N=CH— | H | H | CF₃ | H | CF₃ | H | H |
| CH₃O—N=CH— | H | H | F | H | F | H | F |

TABLE 1-continued

(I)

| R¹ | R² | R³ | R⁴ | R⁵ | R⁶ | R⁷ | R⁸ |
|---|---|---|---|---|---|---|---|
| CH₃O—N=CH— | H | H | F | H | F | H | F |
| CH₃O—CH=N— | CH₃CO | H | F | F | F | F | F |
| CH₃O—N=CH— | CH₃CO | H | Cl | H | Cl | H | Cl |
| CH₃O—N=CH— | CH₃CO | H | Cl | H | Cl | H | H |
| CH₃O—N=CH— | C₂H₅CO | H | Cl | Cl | Cl | H | H |
| CH₃O—N=CH— | C₂H₅O | H | CF₃ | H | CF₃ | H | H |
| CH₃O—N=CH— | C₂H₅CO | H | CF₃ | H | CF₃ | H | CF₃ |
| CH₃O—N=CH— | CF₃CO | H | Cl | H | CF₃ | H | H |
| CH₃O—N=CH— | C₆H₅CO | H | Cl | H | CF₃ | H | Cl |
| CH₃O—N=CH— | ClCH₂CO | H | Cl | H | OCF₃ | H | Cl |
| CH₃O—N=CH— | ICH₂CO | H | Cl | Cl | Cl | H | H |
| CH₃O—N=CH— | BrCH₂CO | H | F | F | F | F | F |
| CH₃O—N=CH— | C₂H₅OCO | H | Cl | H | OCF₃ | H | H |
| CH₃O—N=CH— | CH₃CO | CH₃ | Cl | H | SCF₃ | H | Cl |
| CH₃O—N=CH— | CH₃CO | H | Cl | H | CF₃ | H | Cl |
| CH₃O—N=CH— | C₂H₅CO | H | Cl | H | CF₃ | H | Cl |
| H₂NSO₂— | H | H | CF₃ | H | CF₃ | H | H |
| H₂NSO₂— | H | H | Cl | H | Cl | H | Cl |
| H₂NSO₂— | H | H | Cl | H | Cl | H | H |
| H₃NSO₂— | CH₃CO | H | Cl | Cl | Cl | H | Cl |
| H₂NSO₂— | CH₃CO | H | F | F | F | F | F |
| H₂NSO₂— | CH₃CO | H | F | F | CF₃ | F | F |
| H₂NSO₂— | C₂H₅CO | H | F | F | OCF₃ | F | F |
| H₂NSO₂— | C₂H₅CO | H | F | F | SCF₃ | F | F |
| H₂NSO₂— | C₂H₅CO | H | Cl | H | OCF₃ | H | Cl |
| H₂NSO₂— | CH₃CO | CH₃CO | Cl | H | SCF₃ | H | Cl |
| H₂NSO₂— | CH₃CO | CH₃ | Cl | H | SOCF₃ | H | Cl |
| H₂NSO₂— | ClCH₂CO | H | Cl | H | SO₂CF₃ | H | Cl |
| H₂NSO₂— | BrCH₂CO | H | Cl | H | SO₂CH₃ | H | H |
| H₂NSO₂— | ICH₂CO | H | Cl | H | SO₂CF₃ | H | H |
| H₂NSO₂— | C₆H₅CO | H | Cl | H | CF₃ | H | Cl |
| H₂NSO₂— | C₂H₅CO | H | Cl | H | CF₃ | H | H |
| H₂NSO₂— | CF₃CO | H | Cl | Cl | Cl | H | H |
| H | C₂H₅CO | H | Cl | H | OCF₃ | H | Cl |
| H | CH₃CO | H | Cl | H | OCF₃ | H | Cl |
| H |  | H | Cl | H | OCF₃ | H | Cl |
| H | n-C₃H₇CO | H | Cl | H | OCF₃ | H | Cl |
| H | CH₃OCO | H | Cl | H | OCF₃ | H | Cl |
| H | CH₃OCO | H | Cl | H | SO₂CH₃ | H | Cl |
| H | CH₃CO | H | Cl | H | SO₂CH₃ | H | Cl |
| H | C₂H₅CO | H | Cl | H | SO₂CF₃ | H | Cl |
| H |  | H | Cl | H | SO₂CH₃ | H | Cl |
| H | n-C₃H₇CO | H | Cl | H | SO₂CF₃ | H | Cl |
| H | n-C₃H₇CO | H | Cl | H | SO₂CClF₂ | H | Cl |
| H | CH₃CO | H | Cl | H | SO₂CClF₂ | H | Cl |
| H | C₂H₅CO | H | Cl | H | SO₂CClF₂ | H | Cl |
| H | CH₃CO | H | Br | H | OCF₃ | H | Br |
| H | C₂H₅CO | H | Br | H | OCF₃ | H | H |
| H | n-C₃H₇CO | H | Br | H | OCF₃ | H | H |
| H |  | H | Br | H | OCF₃ | H | H |
| H | CH₃OCO | H | Br | H | OCF₃ | H | H |
| H | CH₃CO | H | Br | H | SCF₃ | H | Br |
| H | CH₃CO | H | Br | H | SCF₃ | H | H |

TABLE 1-continued (I)

| R¹ | R² | R³ | R⁴ | R⁵ | R⁶ | R⁷ | R⁸ |
|---|---|---|---|---|---|---|---|
| H | C₂H₅CO | H | Br | H | SCF₃ | H | H |
| H | n-C₃H₇CO | H | Br | H | SCF₃ | H | H |
| H | C₂H₅CO | H | Cl | H | H | H | Cl |
| H | C₂H₅CO | H | Br | H | Br | H | Br |
| H | C₂H₅CO | H | Cl | H | Cl | H | H |
| H | C₂H₅CO | H | Br | H | Br | H | H |
| NO | C₂H₅CO | H | Cl | H | CF₃ | H | Cl |
| NO | CH₃CO | H | Cl | H | CF₃ | H | Cl |
| NO |  | H | Cl | H | CF₃ | H | Cl |
| NO | CH₃OCO | H | Cl | H | CF₃ | H | Cl |
| NO | n-C₃H₇CO | H | Cl | H | CF₃ | H | Cl |
| NO | CH₃CO | CH₃CO | Cl | H | CF₃ | H | Cl |
| NO | C₂H₅CO | H | Cl | H | OCF₃ | H | H |
| NO |  | H | Cl | H | OCF₃ | H | H |
| NO | n-C₄H₉CO | H | Cl | H | OCF₃ | H | H |
| NO | C₂H₅CO | H | Cl | H | SCF₃ | H | Cl |
| NO | n-C₃H₇CO | H | Cl | H | SCF₃ | H | Cl |
| NO |  | H | Cl | H | SCF₃ | H | Cl |
| NO | CH₃CO | H | Cl | H | SCF₃ | H | Cl |
| NO | CH₃OCO | H | Cl | H | SCF₃ | H | Cl |
| NO | CH₃OCO | H | Cl | H | OCF₃ | H | H |
| NO | C₂H₅CO | H | Cl | Cl | Cl | H | Cl |
| NO | CH₃CO | H | Cl | Cl | Cl | H | Cl |
| NO | CH₃CO | H | Cl | Cl | Cl | H | H |
| NO |  | H | Cl | Cl | Cl | H | Cl |
| NO | CH₃OCO | H | Cl | Cl | Cl | H | Cl |
| NO | CH₃CO | H | Cl | Cl | CF₃ | H | Cl |
| NO | C₂H₅CO | H | Cl | Cl | CF₃ | H | Cl |
| NO | n-C₃H₇CO | H | Cl | Cl | CF₃ | H | Cl |
| NO |  | H | Cl | Cl | CF₃ | H | Cl |
| NO | CH₃OCO | H | Cl | Cl | CF₃ | H | Cl |
| NO | C₂H₅CO | H | Cl | H | OCF₃ | H | Cl |
| NO | CH₃CO | H | Cl | H | OCF₃ | H | Cl |
| NO |  | H | Cl | H | OCF₃ | H | Cl |
| NO | n-C₃H₇CO | H | Cl | H | OCF₃ | H | Cl |
| NO | CH₃OCO | H | Cl | H | OCF₃ | H | Cl |
| NO | CH₃OCO | H | Cl | H | SO₂CF₃ | H | Cl |
| NO | CH₃CO | H | Cl | H | SO₂CF₃ | H | Cl |

TABLE 1-continued

(I)

| $R^1$ | $R^2$ | $R^3$ | $R^4$ | $R^5$ | $R^6$ | $R^7$ | $R^8$ |
|---|---|---|---|---|---|---|---|
| NO | $C_2H_5CO$ | H | Cl | H | $SO_2CF_3$ | H | Cl |
| NO | -CO-H (cyclopropyl) | H | Cl | H | $SO_2CF_3$ | H | Cl |
| NO | $n\text{-}C_3H_7CO$ | H | Cl | H | $SO_2CF_3$ | H | Cl |
| NO | $n\text{-}C_3H_7CO$ | H | Cl | H | $SO_2CClF_2$ | H | Cl |
| NO | $CH_3CO$ | H | Cl | H | $SO_2CClF_2$ | H | Cl |
| NO | $C_2H_5CO$ | H | Cl | H | $SO_2CClF_2$ | H | Cl |
| NO | $CH_3CO$ | H | Br | H | $OCF_3$ | H | Br |
| NO | $C_2H_5CO$ | H | Br | H | $OCF_3$ | H | H |
| NO | $n\text{-}C_3H_7CO$ | H | Br | H | $OCF_3$ | H | H |
| NO | -CO-H (cyclopropyl) | H | Br | H | $OCF_3$ | H | H |
| NO | $CH_3OCO$ | H | Br | H | $OCF_3$ | H | H |
| NO | $CH_3CO$ | H | Br | H | $SCF_3$ | H | Br |
| NO | $CH_3CO$ | H | Br | H | $SCF_3$ | H | Br |
| NO | $C_2H_5CO$ | H | Br | H | $SCF_3$ | H | H |
| NO | $n\text{-}C_3H_7CO$ | H | Br | H | $SCF_3$ | H | H |
| NO | $C_2H_5CO$ | H | Cl | H | H | H | Cl |
| NO | $C_2H_5CO$ | H | Br | H | Br | H | Br |
| NO | $C_2H_5CO$ | H | Cl | H | Cl | H | H |
| NO | $C_2H_5CO$ | H | Br | H | Br | H | H |
| $NO_2$ | $C_2H_5CO$ | H | Cl | H | $OCF_3$ | H | Cl |
| $NO_2$ | $CH_3CO$ | H | Cl | H | $OCF_3$ | H | Cl |
| $NO_2$ | -CO-H (cyclopropyl) | H | Cl | H | $OCF_3$ | H | Cl |
| $NO_2$ | $n\text{-}C_3H_7CO$ | H | Cl | H | $OCF_3$ | H | Cl |
| $NO_2$ | $CH_3OCO$ | H | Cl | H | $OCF_3$ | H | Cl |
| $NO_2$ | $CH_3OCO$ | H | Cl | H | $SO_2CF_3$ | H | Cl |
| $NO_2$ | $CH_3CO$ | H | Cl | H | $SO_2CF_3$ | H | Cl |
| $NO_2$ | $C_2H_5CO$ | H | Cl | H | $SO_2CF_3$ | H | Cl |
| $NO_2$ | cyclopropyl-CO-H | H | Cl | H | $SO_2CF_3$ | H | Cl |
| $NO_2$ | $n\text{-}C_3H_7CO$ | H | Cl | H | $SO_2CF_3$ | H | Cl |
| $NO_2$ | $n\text{-}C_3H_7CO$ | H | Cl | H | $SO_2CClF_2$ | H | Cl |
| $NO_2$ | $CH_3CO$ | H | Cl | H | $SO_2CClF_2$ | H | Cl |
| $NO_2$ | $C_2H_5CO$ | H | Cl | H | $SO_2CClF_2$ | H | Cl |
| $NO_2$ | $CH_3CO$ | H | Br | H | $OCF_3$ | H | Br |
| $NO_2$ | $C_2H_5CO$ | H | Br | H | $OCF_3$ | H | H |
| $NO_2$ | $n\text{-}C_3H_7CO$ | H | Br | H | $OCF_3$ | H | H |
| $NO_2$ | cyclopropyl-CO-H | H | Br | H | $OCF_3$ | H | H |
| $NO_2$ | $CH_3OCO$ | H | Br | H | $OCF_3$ | H | H |
| $NO_2$ | $CH_3CO$ | H | Br | H | $SCF_3$ | H | Br |
| $NO_2$ | $CH_3CO$ | H | Br | H | $SCF_3$ | H | H |
| $NO_2$ | $C_2H_5CO$ | H | Br | H | $SCF_3$ | H | H |
| $NO_2$ | $n\text{-}C_3H_7CO$ | H | Br | H | $SCF_3$ | H | H |
| $NO_2$ | $C_2H_5CO$ | H | Cl | H | H | H | Cl |
| $NO_2$ | $C_2H_5CO$ | H | Br | H | Br | H | Br |

TABLE 1-continued (I)

| R¹ | R² | R³ | R⁴ | R⁵ | R⁶ | R⁷ | R⁸ |
|---|---|---|---|---|---|---|---|
| NO₂ | C₂H₅CO | H | Cl | H | Cl | H | H |
| NO₂ | C₂H₅CO | H | Br | H | Br | H | H |
| NO₂ | C₂H₅CO | H | Cl | H | CF₃ | H | Cl |
| NO₂ | CH₃CO | H | Cl | H | CF₃ | H | Cl |
| NO₂ | cyclopropyl-CO-H | H | Cl | H | CF₃ | H | Cl |
| NO₂ | CH₃OCO | H | Cl | H | CF₃ | H | Cl |
| NO₂ | n-C₃H₇CO | H | Cl | H | CF₃ | H | Cl |
| NO₂ | CH₃CO | CH₃CO | Cl | H | CF₃ | H | Cl |
| NO₂ | C₂H₅CO | H | Cl | H | OCF₃ | H | H |
| NO₂ | cyclopropyl-CO-H | H | Cl | H | OCF₃ | H | H |
| NO₂ | n-C₄H₉CO | H | Cl | H | OCF₃ | H | H |
| NO₂ | C₂H₅CO | H | Cl | H | SCF₃ | H | Cl |
| NO₂ | n-C₃H₇CO | H | Cl | H | SCF₃ | H | Cl |
| NO₂ | cyclopropyl-CO-H | H | Cl | H | SCF₃ | H | Cl |
| NO₂ | CH₃CO | H | Cl | H | SCF₃ | H | Cl |
| NO₂ | CH₃OCO | H | Cl | H | SCF₃ | H | Cl |
| NO₂ | CH₃OCO | H | Cl | H | OCF₃ | H | H |
| NO₂ | C₂H₅CO | H | Cl | Cl | Cl | H | Cl |
| NO₂ | CH₃CO | H | Cl | Cl | Cl | H | Cl |
| NO₂ | CH₃CO | H | Cl | Cl | Cl | H | H |
| NO₂ | cyclopropyl-CO-H | H | Cl | Cl | Cl | H | Cl |
| NO₂ | CH₃OCO | H | Cl | Cl | Cl | H | Cl |
| NO₂ | CH₃CO | H | Cl | Cl | CF₃ | H | Cl |
| NO₂ | C₂H₅CO | H | Cl | Cl | CF₃ | H | Cl |
| NO₂ | n-C₃H₇CO | H | Cl | Cl | CF₃ | H | Cl |
| NO₂ | cyclopropyl-CO-H | H | Cl | Cl | CF₃ | H | Cl |
| NO₂ | CH₃OCO | H | Cl | Cl | CF₃ | H | Cl |
| PO(OC₂H₅)₂ | C₂H₅CO | H | Cl | H | CF₃ | H | Cl |
| PO(OC₂H₅)₂ | CH₃CO | H | Cl | H | CF₃ | H | Cl |
| PO(OC₂H₅)₂ | cyclopropyl-CO-H | H | Cl | H | CF₃ | H | Cl |
| PO(OC₂H₅)₂ | CH₃CO | H | Cl | H | CF₃ | H | Cl |
| PO(OC₂H₅)₂ | n-C₃H₇CO | H | Cl | H | CF₃ | H | Cl |
| PO(OC₂H₅)₂ | CH₃CO | CH₃CO | Cl | H | CF₃ | H | Cl |
| PO(OC₂H₅)₂ | C₂H₅CO | H | Cl | H | OCF₃ | H | H |

TABLE 1-continued

(I)

| R¹ | R² | R³ | R⁴ | R⁵ | R⁶ | R⁷ | R⁸ |
|---|---|---|---|---|---|---|---|
| PO(OC$_2$H$_5$)$_2$ | cyclopropyl-CO-H | H | Cl | H | OCF$_3$ | H | H |
| PO(OC$_2$H$_5$)$_2$ | n-C$_4$H$_9$CO | H | Cl | H | OCF$_3$ | H | H |
| PO(OC$_2$H$_5$)$_2$ | C$_2$H$_5$CO | H | Cl | H | SCF$_3$ | H | Cl |
| PO(OC$_2$H$_5$)$_2$ | n-C$_3$H$_7$CO | H | Cl | H | SCF$_3$ | H | Cl |
| PO(OC$_2$H$_5$)$_2$ | cyclopropyl-CO-H | H | Cl | H | SCF$_3$ | H | Cl |
| PO(OC$_2$H$_5$)$_2$ | CH$_3$CO | H | Cl | H | SCF$_3$ | H | Cl |
| PO(OC$_2$H$_5$)$_2$ | CH$_3$OCO | H | Cl | H | SCF$_3$ | H | Cl |
| PO(OC$_2$H$_5$)$_2$ | CH$_3$OCO | H | Cl | H | OCF$_3$ | H | H |
| PO(OC$_2$H$_5$)$_2$ | C$_2$H$_5$CO | H | Cl | Cl | Cl | H | Cl |
| PO(OC$_2$H$_5$)$_2$ | CH$_3$CO | H | Cl | Cl | Cl | H | H |
| PO(OC$_2$H$_5$)$_2$ | CH$_3$CO | H | Cl | Cl | Cl | H | H |
| PO(OC$_2$H$_5$)$_2$ | cyclopropyl-CO-H | H | Cl | Cl | Cl | H | Cl |
| PO(OC$_2$H$_5$)$_2$ | CH$_3$CO | H | Cl | Cl | Cl | H | Cl |
| PO(OC$_2$H$_5$)$_2$ | CH$_3$CO | H | Cl | Cl | CF$_3$ | H | Cl |
| PO(OC$_2$H$_5$)$_2$ | C$_2$H$_5$CO | H | Cl | Cl | CF$_3$ | H | Cl |
| PO(OC$_2$H$_5$)$_2$ | —C$_3$H$_7$CO | H | Cl | Cl | CF$_3$ | H | Cl |
| PO(OC$_2$H$_5$)$_2$ | cyclopropyl-CO-H | H | Cl | Cl | CF$_3$ | H | Cl |
| PO(OC$_2$H$_5$)$_2$ | C$_2$H$_5$CO | H | Cl | Cl | CF$_3$ | H | Cl |
| PO(OC$_2$H$_5$)$_2$ | C$_2$H$_5$CO | H | Cl | H | OCF$_3$ | H | Cl |
| PO(OC$_2$H$_5$)$_2$ | CH$_3$CO | Cl | Cl | H | OCF$_3$ | H | Cl |
| PO(OC$_2$H$_5$)$_2$ | cyclopropyl-CO-H | H | Cl | H | OCF$_3$ | H | Cl |
| PO(OC$_2$H$_5$)$_2$ | n-C$_3$H$_7$CO | H | Cl | H | OCF$_3$ | H | Cl |
| PO(OC$_2$H$_5$)$_2$ | CH$_3$OCO | H | Cl | H | OCF$_3$ | H | Cl |
| PO(OC$_2$H$_5$)$_2$ | CH$_3$OCO | H | Cl | H | SO$_2$CF$_3$ | H | Cl |
| PO(OC$_2$H$_5$)$_2$ | CH$_3$CO | H | Cl | H | SO$_2$CF$_3$ | H | Cl |
| PO(OC$_2$H$_5$)$_2$ | C$_2$H$_5$CO | H | Cl | H | SO$_2$CF$_3$ | H | Cl |
| PO(OC$_2$H$_5$)$_2$ | cyclopropyl-CO-H | H | Cl | H | SO$_3$CF$_3$ | H | Cl |
| PO(OC$_2$H$_5$)$_2$ | n-C$_3$H$_7$CO | H | Cl | H | SO$_2$CF$_3$ | H | Cl |
| PO(OC$_2$H$_5$)$_2$ | n-C$_3$H$_7$CO | H | Cl | H | SO$_2$CClF$_2$ | H | Cl |
| PO(OC$_2$H$_5$)$_2$ | CH$_3$CO | H | Cl | H | SO$_2$CClF$_2$ | H | Cl |
| PO(OC$_2$H$_5$)$_2$ | C$_2$H$_5$CO | H | Cl | H | SO$_2$CClF$_2$ | H | Cl |
| PO(OC$_2$H$_5$)$_2$ | CH$_3$CO | H | Br | H | OCF$_3$ | H | Br |
| PO(OC$_2$H$_5$)$_2$ | C$_2$H$_5$O | H | Br | H | OCF$_3$ | H | H |
| PO(OC$_2$H$_5$)$_2$ | n-C$_3$H$_7$CO | H | Br | H | OCF$_3$ | H | H |
| PO(OC$_2$H$_5$)$_2$ | cyclopropyl-CO-H | H | Br | H | OCF$_3$ | H | H |

TABLE 1-continued

| R¹ | R² | R³ | R⁴ | R⁵ | R⁶ | R⁷ | R⁸ |
|---|---|---|---|---|---|---|---|
| PO(OC$_2$H$_5$)$_2$ | CH$_3$OCO | H | Br | H | OCF$_3$ | H | H |
| PO(OC$_2$H$_5$)$_2$ | CH$_3$CO | H | Br | H | SCF$_3$ | H | Br |
| PO(OC$_2$H$_5$)$_2$ | CH$_3$CO | H | Br | H | SCF$_3$ | H | H |
| PO(OC$_2$H$_5$)$_2$ | C$_2$H$_5$CO | H | Br | H | SCF$_3$ | H | H |
| PO(OC$_2$H$_5$)$_2$ | n-C$_3$H$_7$CO | H | Br | H | SCF$_3$ | H | H |
| PO(OC$_2$H$_5$)$_2$ | C$_2$H$_5$CO | H | Cl | H | H | H | Cl |
| PO(OC$_2$H$_5$)$_2$ | C$_2$H$_5$O | H | Br | H | Br | H | Br |
| PO(OC$_2$H$_5$)$_2$ | C$_2$H$_5$CO | H | Cl | H | Cl | H | H |
| PO(OC$_2$H$_5$)$_2$ | C$_2$H$_5$CO | H | Br | H | Br | H | H |
| Cl | C$_2$H$_5$CO | H | Cl | H | CF$_3$ | H | Cl |
| Cl | CH$_3$CO | H | Cl | H | CF$_3$ | H | Cl |
| Cl | cyclopropyl-CO- | H | Cl | H | CF$_3$ | H | Cl |
| Cl | CH$_3$OCO | H | Cl | H | CF$_3$ | H | Cl |
| Cl | n-C$_3$H$_7$CO— | H | Cl | H | CF$_3$ | H | Cl |
| Cl | CH$_3$CO | CH$_3$CO | Cl | H | CF$_3$ | H | Cl |
| Cl | C$_2$H$_5$CO | H | Cl | H | OCF$_3$ | H | H |
| Cl | cyclopropyl-CO- | H | Cl | H | OCF$_3$ | H | H |
| Cl | n-C$_4$H$_9$CO | H | Cl | H | OCF$_3$ | H | H |
| Cl | C$_2$H$_5$CO | H | Cl | H | SCF$_3$ | H | Cl |
| Cl | n-C$_3$H$_7$CO | H | Cl | H | SCF$_3$ | H | Cl |
| Cl | cyclopropyl-CO- | H | Cl | H | SCF$_3$ | H | Cl |
| Cl | CH$_3$CO | H | Cl | H | SCF$_3$ | H | Cl |
| Cl | CH$_3$OCO | H | Cl | H | SCF$_3$ | H | Cl |
| Cl | CH$_3$OCO | H | Cl | H | OCF$_3$ | H | H |
| Cl | C$_2$H$_5$CO | H | Cl | Cl | Cl | H | Cl |
| Cl | CH$_3$CO | H | Cl | Cl | Cl | H | Cl |
| Cl | CH$_3$CO | H | Cl | Cl | Cl | H | H |
| Cl | cyclopropyl-CO- | H | Cl | Cl | Cl | H | Cl |
| Cl | CH$_3$OCO | H | Cl | Cl | Cl | H | Cl |
| Cl | CH$_3$CO | H | Cl | Cl | CF$_3$ | H | Cl |
| Cl | C$_2$H$_5$CO | H | Cl | Cl | CF$_3$ | H | Cl |
| Cl | n-C$_3$H$_7$CO | H | Cl | Cl | CF$_3$ | H | Cl |
| Cl | cyclopropyl-CO- | H | Cl | Cl | CF$_3$ | H | Cl |
| Cl | CH$_3$OCO | H | Cl | Cl | CF$_3$ | H | Cl |
| Cl | C$_2$H$_5$CO | H | Cl | H | OCF$_3$ | H | Cl |
| Cl | CH$_3$CO | H | Cl | H | OCF$_3$ | H | Cl |
| Cl | cyclopropyl-CO- | H | Cl | H | OCF$_3$ | H | Cl |

TABLE 1-continued (I)

| $R^1$ | $R^2$ | $R^3$ | $R^4$ | $R^5$ | $R^6$ | $R^7$ | $R^8$ |
|---|---|---|---|---|---|---|---|
| Cl | n-$C_3H_7$CO | H | Cl | H | $OCF_3$ | H | Cl |
| Cl | $CH_3$OCO | H | Cl | H | $OCF_3$ | H | Cl |
| Cl | $CH_3$OCO | H | Cl | H | $SO_2CF_3$ | H | Cl |
| Cl | $CH_3$CO | H | Cl | H | $SO_2CF_3$ | H | Cl |
| Cl | $C_2H_5$CO | H | Cl | H | $SO_2CF_3$ | H | Cl |
| Cl | cyclopropyl-CO-H | H | Cl | H | $SO_2CF_3$ | H | Cl |
| Cl | n-$C_3H_7$CO | H | Cl | H | $SO_2CF_3$ | H | Cl |
| Cl | n-$C_3H_7$CO | H | Cl | H | $SO_2CClF_2$ | H | Cl |
| Cl | $CH_3$CO | H | Cl | H | $SO_2CClF_2$ | H | Cl |
| Cl | $C_2H_5$CO | H | Cl | H | $SO_2CClF_2$ | H | Cl |
| Cl | $CH_3$CO | H | Br | H | $OCF_3$ | H | Br |
| Cl | $C_2H_5$CO | H | Br | H | $OCF_3$ | H | H |
| Cl | n-$C_3H_7$CO | H | Br | H | $OCF_3$ | H | H |
| Cl | cyclopropyl-CO-H | H | Br | H | $OCF_3$ | H | H |
| Cl | $CH_3$OCO | H | Br | H | $OCF_3$ | H | H |
| Cl | $CH_3$CO | H | Br | H | $SCF_3$ | H | Br |
| Cl | $CH_3$CO | H | Br | H | $SCF_3$ | H | H |
| Cl | $C_2H_5$CO | H | Br | H | $SCF_3$ | H | H |
| Cl | n-$C_3H_7$CO | H | Br | H | $SCF_3$ | H | H |
| Cl | $C_2H_5$CO | H | Cl | H | H | H | Cl |
| Cl | $C_2H_5$CO | H | Br | H | Br | H | Br |
| Cl | $C_2H_5$CO | H | Cl | H | Cl | H | H |
| Cl | $C_2H_5$CO | H | Br | H | Br | H | H |
| H | H—CO— | H | Cl | H | Cl | H | Cl |
| H | H—CO— | H | Cl | Cl | Cl | H | H |
| H | H—CO— | H | Cl | H | $OCF_3$ | H | Cl |
| H | H—CO— | H | Cl | H | $SCF_3$ | H | Cl |
| H | H—CO— | H | Cl | H | $OCF_3$ | H | H |
| H | H—CO— | H | Cl | H | $CF_3$ | H | Cl |
| H | H—CO— | H | Br | H | Br | H | Br |
| H | H—CO— | H | Cl | H | Br | H | Cl |
| H | H—CO— | H | Cl | H | $SO_2CF_3$ | H | H |
| H | H—CO— | H | Cl | H | $SO_2CF_3$ | H | Cl |
| $NO_2$ | H—CO— | H | Cl | H | Cl | H | Cl |
| $NO_2$ | H—CO— | H | Cl | Cl | Cl | H | H |
| $NO_2$ | H—CO— | H | Cl | H | $OCF_3$ | H | Cl |
| $NO_2$ | H—CO— | H | Cl | H | $OCF_3$ | H | H |
| $NO_2$ | H—CO— | H | Cl | H | $SCF_3$ | H | Cl |
| $NO_2$ | H—CO— | H | Cl | H | $SCF_3$ | H | H |
| $NO_2$ | H—CO— | H | Cl | H | $SO_2CF_3$ | H | H |
| $NO_2$ | H—CO— | H | Cl | H | $SO_2CF_3$ | H | Cl |
| $NO_2$ | H—CO— | H | Br | H | Br | H | Br |
| $NO_2$ | H—CO— | H | Cl | H | Br | H | Cl |
| $NO_2$ | H—CO— | H | Cl | H | Br | H | Br |
| $NO_2$ | H—CO— | H | Br | H | $OCF_3$ | H | Br |
| $NO_2$ | H—CO— | H | Br | H | $OCF_3$ | H | H |
| $NO_2$ | H—CO— | H | Br | H | $SCF_3$ | H | Br |
| $NO_2$ | H—CO— | H | I | H | $OCF_3$ | H | H |
| $NO_2$ | $CH_3$CO | H | Cl | H | Cl | H | Cl |
| $NO_2$ | $CH_3$CO | H | Cl | Cl | Cl | H | H |
| $NO_2$ | $CH_3$CO | H | Cl | H | $OCF_3$ | H | Cl |
| $NO_2$ | $CH_3$CO | H | Br | H | Br | H | Br |
| $NO_2$ | $CH_3$CO | H | Cl | H | Br | H | Cl |
| $NO_2$ | $CH_3$CO | H | Cl | H | Br | H | Br |
| $NO_2$ | $CH_3$CO | H | Br | H | Cl | H | Cl |
| $NO_2$ | $CH_3$CO | H | Br | H | $OCF_3$ | H | H |
| $NO_2$ | $CH_3$CO | H | Br | H | $OCF_3$ | H | Br |
| $NO_2$ | $CH_3$CO | H | Br | H | $SCF_3$ | H | H |

TABLE 1-continued (I)

| R¹ | R² | R³ | R⁴ | R⁵ | R⁶ | R⁷ | R⁸ |
|---|---|---|---|---|---|---|---|
| NO₂ | CH₃CO | H | Br | H | SCF₃ | H | Br |
| NO₂ | CH₃CO | H | Br | H | SO₂CH₃ | H | H |
| NO₂ | CH₃CO | H | Br | H | SO₂CF₃ | H | Br |
| NO₂ | CH₃CO | H | Br | H | SO₂CF₃Cl | H | H |
| NO₂ | CH₃CO | H | Br | H | SO₂CF₂Cl | H | Br |
| NO₂ | CH₃CO | H | Cl | H | OCF₂Cl | H | H |
| NO₂ | CH₃CO | H | Cl | H | OCF₂CHF₂ | H | Cl |
| NO₂ | CH₃CO | H | Cl | H | OCHF₂ | H | H |
| NO₂ | CH₃CO | H | Cl | H | OCHF₂ | H | Cl |
| NO₂ | CH₃CO | H | Cl | H | OCH₂CF₃ | H | H |
| NO₂ | CH₃CO | H | Cl | H | OCH₂CF₃ | H | Cl |
| NO₂ | CH₃CO | H | Br | H | OCH₂CF₃ | H | H |
| NO₂ | CH₃CO | H | Br | H | OCH₂CF₃ | H | Br |
| NO₂ | CH₃CO | H | Br | H | CF₃ | H | H |
| NO₂ | CH₃CO | H | Br | H | CF₃ | H | Br |
| NO₂ | C₂H₅CO | H | Cl | H | OCHF₂ | H | Cl |
| NO₂ | C₂H₅CO | H | Cl | H | OCHF₂ | H | H |
| NO₂ | C₂H₅CO | H | Cl | H | OCF₂CHF₂ | H | H |
| NO₂ | C₂H₅CO | H | Cl | H | OCF₂CHF₂ | H | Cl |
| NO₂ | C₂H₅CO | H | Cl | H | CHF₂ | H | H |
| NO₂ | C₂H₅CO | H | Cl | H | CHF₂ | H | Cl |
| NO₂ | C₂H₅CO | H | Cl | H | OCF₂CHFCl | H | H |
| NO₂ | C₂H₅CO | H | Cl | H | OCF₂CHFCl | H | Cl |
| NO₂ | C₂H₅CO | H | Cl | H | Br | H | Cl |

Some of the substituted 5-amino-1-phenylpyrazoles of the formula (I) which are to be used according to the invention are known (see: J.Org.Chem. 36,2972–2974 [1971]; J.Heterocycl.Chem. 7, 345–349 [1970] and C.A. 62: 13137c).

Substituted 5-amino-1-phenyl-pyrazoles which were hitherto unknown are those of the formula (I')

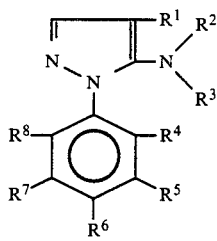

(I')

in which R¹, R², R³, R⁴, R⁵, R⁶, R⁷ and R⁸ have the meaning given above, except that, when R¹ represents hydrogen, methyl or optionally substitued phenyl, R⁴ and R⁶ cannot simultaneously represent the nitro group.

The hitherto unknown substituted 5-amino-1-phenyl-pyrazoles of the formula (I') are obtained if (a) phenylhydrazines of the formula (II)

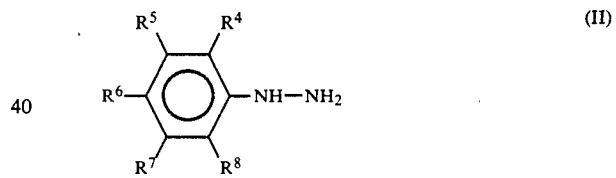

(II)

in which R⁴, R⁵, R⁶, R⁷ and R⁸ have the meaning given above, are reacted with acrylonitrile derivatives of the formula (III)

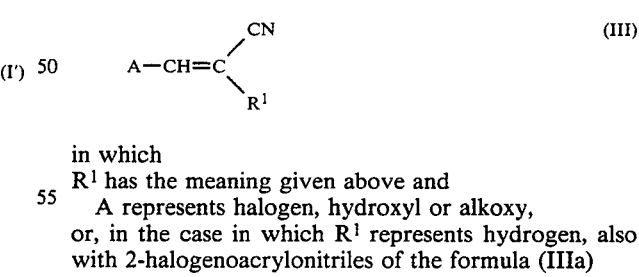

(III)

in which
R¹ has the meaning given above and
A represents halogen, hydroxyl or alkoxy,
or, in the case in which R¹ represents hydrogen, also with 2-halogenoacrylonitriles of the formula (IIIa)

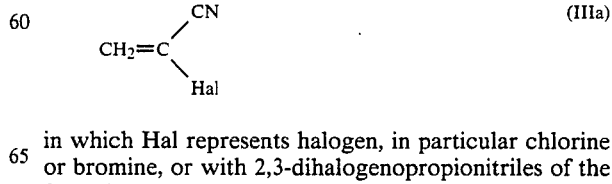

(IIIa)

in which Hal represents halogen, in particular chlorine or bromine, or with 2,3-dihalogenopropionitriles of the formula (IIIb)

$$\text{Hal}'-CH_2-CH\diagup^{CN}_{\diagdown \text{Hal}'} \tag{IIIb}$$

in which Hal' represents halogen, in particular chlorine or bromine, the reaction either being carried out to give the phenylhydrazine derivatives of the formula (IV)

$$\begin{array}{c} R^5 \quad R^4 \\ R^6-\bigcirc-NH-NH-Z \\ R^7 \quad R^8 \end{array} \tag{IV}$$

(new substances)

in which
$R^4$, $R^5$, $R^6$, $R^7$ and $R^8$ have the meaning given under formula (I') and
Z represents one of the radicals $$-CH=C\diagup^{CN}_{\diagdown R^1}, \quad -CH_2-CH\diagup^{CN}_{\diagdown \text{Hal}} \quad \text{or} \quad -CH_2-CH\diagup^{CN}_{\diagdown \text{Hal}'}$$

wherein Hal and Hal' represent identical or different halogen atoms, in a first stage, if appropriate in the presence of a diluent, and if appropriate in the presence of a reaction auxiliary, the product being subjected to a cyclization reaction in a second stage, if appropriate in the presence of a diluent and, if appropriate, in the presence of an acid-binding agent, or cyclization being carried out directly in one reaction step without isolation of the intermediate of the formula (IV), if appropriate in the presence of a diluent, to give the 5-amino-pyrazoles of the formula (Ia).

$$\begin{array}{c} \overset{R^1}{\underset{N_{\diagdown N}}{\parallel}}\diagdown_{NH_2} \\ R^8-\bigcirc-R^4 \\ R^7 \quad R^5 \\ R^6 \end{array} \tag{Ia}$$

in which $R^1$, $R^4$, $R^5$, $R^6$, $R^7$ and $R^8$ have the meaning given above, or if
(b) the 5-amino-pyrazoles of the formula (Ia)

$$\begin{array}{c} \overset{R^1}{\underset{N_{\diagdown N}}{\parallel}}\diagdown_{NH_2} \\ R^8-\bigcirc-R^4 \\ R^7 \quad R^5 \\ R^6 \end{array} \tag{Ia}$$

in which $R^1$, $R^4$, $R^5$, $R^6$, $R^7$ and $R^8$ have the above meaning, which are obtainable by process (a) are re-acted in a generally customary manner with acylating agents or alkylating agents of the formula (V)

$$R^{14}-A' \tag{V}$$

in which
$R^{14}$ represents alkyl or a radical $$\overset{X}{\underset{\parallel}{-C-R^{12}}},$$

wherein
X and $R^{12}$ have the above meaning, and
A' represents an electron-attracting leaving group, or with iso(thio)cyanates of the formula (VI)

$$R^{15}-N=C=X \tag{VI}$$

in which
$R^{15}$ represents alkyl or optionally substituted aryl and
X has the above meaning,
if appropriate in the presence of a diluent, and if appropriate in the presence of an acid-binding agent, to give the 5-amino-pyrazoles alkylated or acylated at the nitrogen, of the formula (Ib)

$$\begin{array}{c} \overset{R^1}{\underset{N_{\diagdown N}}{\parallel}}\diagdown N\diagup^{R^2}_{\diagdown R^{3'}} \\ R^8-\bigcirc-R^4 \\ R^7 \quad R^5 \\ R^6 \end{array} \tag{Ib}$$

in which
$R^1$, $R^2$, $R^4$, $R^5$, $R^6$, $R^7$ and $R^8$ have the above meaning and
$R^{3'}$ represents the same radicals as $R^3$ given above, with the exception of the hydrogen radical, or if
(c) the 5-amino-pyrazoles of the formula (Ic)

$$\begin{array}{c} \overset{}{\underset{N_{\diagdown N}}{\parallel}}\diagdown N\diagup^{R^2}_{\diagdown R^3} \\ R^8-\bigcirc-R^4 \\ R^7 \quad R^5 \\ R^6 \end{array} \tag{Ic}$$

in which $R^2$, $R^3$, $R^4$, $R^5$, $R^6$, $R^7$ and $R^8$ have the above meaning, which are unsubstituted in the 4-position and are obtainable by process (a) or (b), are substituted in the 4-position, likewise in a generally customary manner, using electrophilic agents of the formula (VII)

$$R^{1'}-E \tag{VII}$$

in which $R^{1'}$ represents halogen, nitroso, nitro, alkyl, formyl, alkanoyl, aroyl, hydroxysulphonyl or chlorosulphonyl and E represents an electron-attracting leaving grouping, or using other customary electrophilic reagents, if appropriate in the presence of a diluent and, if appropriate, in the presence of a catalyst or a reaction auxiliary, or if (d) the 4-chlorosulphonyl-5-amino-pyrazoles obtainable by process (c) of the formula (Id)

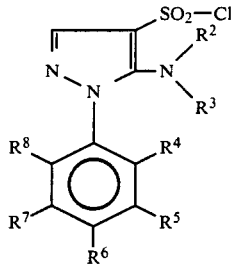

(Id)

in which $R^2$, $R^3$, $R^4$, $R^5$, $R^6$, $R^7$ and $R^8$ have the above meaning, are substituted at the chlorosulphonyl group in the 4-position, using amines of the formula (VIII)

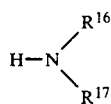

(VIII)

in which $R^{16}$ and $R^{17}$ independently of one another represent hydrogen or alkyl, or using an alkali metal fluoride of the formula (IX)

$Me^{\oplus} F^{\ominus}$ (IX)

in which $Me^{\oplus}$ represents an alkali metal cation, if appropriate in the presence of a diluent and, if appropriate, in the presence of an acid-binding agent, or if (e) the 4-acyl-5-amino-pyrazoles of the formula (Ie)

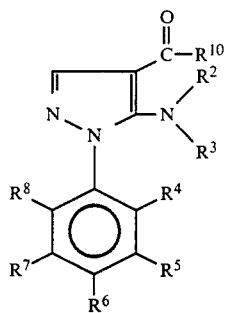

(Ie)

in which $R^2$, $R^3$, $R^4$, $R^5$, $R^6$, $R^7$, $R^8$ and $R^{10}$ have the above meaning, which are obtainable by the process (c) or (f), are reacted with hydroxylamine derivatives of the formula (X)

$H_2N-OR^{11}$ (X)

in which $R^{11}$ has the meaning given above, or with their hydrogen halide addition salts such as hydrochlorides (HCL salts), if appropriate in the presence of a diluent and, if appropriate, in the presence of an acid-binding agent, or if (f) 4-cyano-5-amino-pyrazoles of the formula (XI)

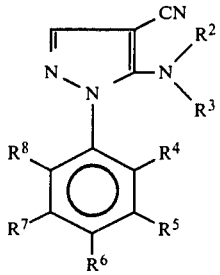

(XI)

in which $R^2$, $R^3$, $R^4$, $R^5$, $R^6$, $R^7$ and $R^8$ have the meaning given above, are reacted with formic acid and Raney nickel to give the corresponding 5-amino-4-formyl-pyrazoles of the formula (If)

(If)

in which $R^2$, $R^3$, $R^4$, $R^5$, $R^6$, $R^7$ and $R^8$ have the meaning given above.

If, for example, 2-chloroacrylonitrile and 2,6-dichloro-4-trifluoromethyl-phenylhydrazine are used as starting materials, the course of the reaction of preparation process (a) can be represented by the following equation:

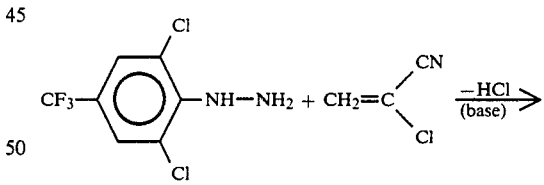

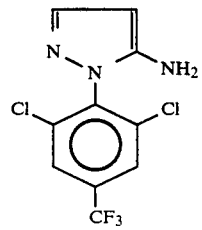

If, for example, 5-amino-1-(2,4,6-trichlorophenyl)-pyrazole and propionyl chloride are used as starting materials, the course of the reaction of preparation process (b) can be represented by the following equation:

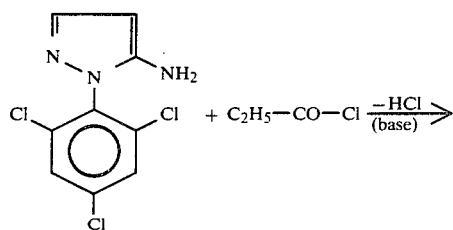

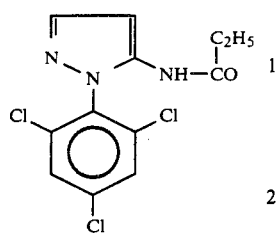

If, for example, 5-propionamido-1-(2,3,4-trichlorophenyl)-pyrazole and nitric acid are used as starting materials, the course of the reaction of preparation process (c) can be represented by the following equation:

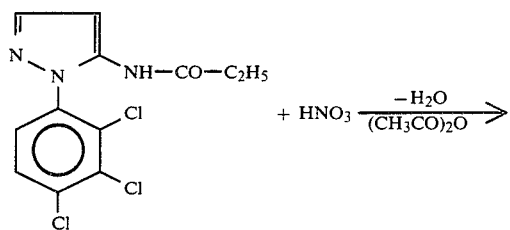

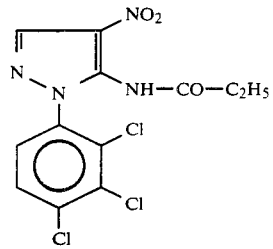

If, for example, 5-acetamido-4-chlorosulphonyl-1-(2,4,6-trichlorophenyl)-pyrazole and diethylamine are used as starting materials, the course of the reaction of preparation process (d) can be represented by the following equation:

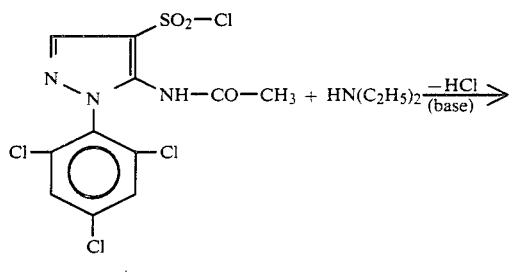

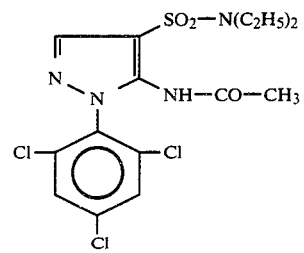

If, for example, 5-acetamido-4-acetyl-1-(pentafluorophenyl)-pyrazole and 0-methyl-hydroxylamine hydrochloride are used as starting materials, the course of the reaction of preparation process (e) can be represented by the following equation:

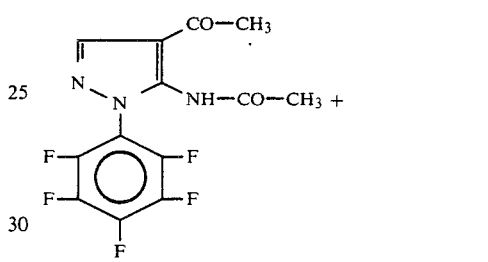

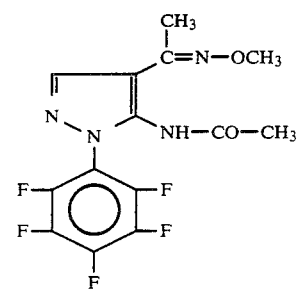

If, for example, 5-amino-4-cyano-1-(2,3,4-trichlorophenyl)-pyrazole and formic acid are used as starting material, and Raney nickel is used as a reducing agent, the course of the reaction of process (f) according to the invention can be represented by the following equation:

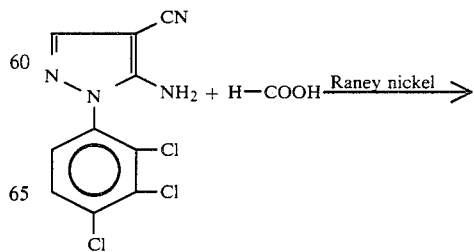

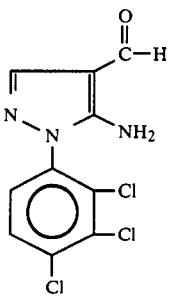

Formula (II) gives a general definition of the phenylhydrazines required as starting materials for carrying out preparation process (a) according to the invention. In this formula (II), $R^4$, $R^5$, $R^6$, $R^7$ and $R^8$ preferably represent those substituents which have already been mentioned in the description of the substances which can be used according to the invention, of the formula (I), as being preferred for these radicals.

The majority of the phenylhydrazines of the formula (II) are known or can be prepared by known processes in a simple, analogous manner (see: for example, HoubenWeyl "Methoden der organischen Chemie" (Methods of organic chemistry), Volume X,2, page 203, Thieme Verlag Stuttgart 1967) by, for example, reacting the known anilines of the formula (XII)

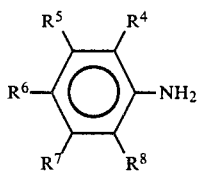

in which $R^4$, $R^5$, $R^6$, $R^7$ and $R^8$ have the meaning given above, with sodium nitrite, in the presence of an acid, such as, for example, sulphuric acid, and then with tin(II) chloride, likewise in the presence of an acid, such as, for example, hydrochloric acid, at temperatures between $-20°$ C. and $+80°$ C.

Formula (III) gives a general definition of the acrylonitrile derivatives furthermore required as starting materials for carrying out preparation process (a). In this formula (III), $R^1$ preferably represents those radicals which have already been mentioned in the description of the substances which can be used according to the invention, of the formula (I), as being preferred for these substituents. A preferably represents chlorine or bromine, hydroxyl, methoxy or ethoxy. The acrylonitrile derivatives of the formula (III) are known (see: for example, DE-OS (German Published Specification) 3,129,429, European Pat. No. 34,945; J.Chem.Soc. D 1970, 1255; Can.J.Chem. 48, 2104–2109 (1970); J.Heterocyclic Chem. 19, 1267–1273 (1982); and Can.J.-Chem. 51, 1239–1244 [1973]), or can be obtained by processes known from the literature in a simple analogous manner. The 2-halogeno-acrylonitriles of the formula (IIIa) and the 2,3-dihalogeno-propionitriles of the formula (IIIb) are likewise known (see, for example, J.Prakt. Chemie 321, 93 [1979]; J. Heterocyclic Chem. 19, 1265 [1982]; and J. Heterocyclic Chem. 19, 1267 [1982]).

Formula (Ia) gives a general definition of the 5-amino-pyrazoles required as starting materials for carrying out preparation process (b). In this formula (Ia), $R^1$, $R^4$, $R^5$, $R^6$, $R^7$ and $R^8$ preferably represent those radicals which have already been mentioned in the description of the substances which can be used according to the invention, of the formula (I), as being preferred for these radicals.

The 5-amino-pyrazoles of the formula (Ia) were hitherto unknown. They are obtained by preparation process (a).

Formula (V) gives a general definition of the alkylating and acylating agents furthermore required as starting materials for carrying out preparation process (b). In this formula (V), $R^{14}$ preferably represents a straight-chain or branched alkyl having up to 4 carbon atoms, and furthermore represents a radical —C, wherein X and $R^{12}$ preferably represent those radicals which have already been mentioned for these radicals, in the description of the substances which can be used according to the invention, of the formula (I). A' preferably represents chlorine, bromine or iodine, p-toluenesulphonyloxy, alkoxysulphonyloxy or acyloxy. The alkylating and acylating agents of the formula (V) are generally known compounds of organic chemistry.

Formula (VI) gives a general definition of the iso(thio)cyanates which can alternatively be used as starting materials for carrying out preparation process (b). In this formula, X preferably represents oxygen or sulphur, and $R^{15}$ preferably represents straight-chain or branched alkyl having up to 4 carbon atoms, or phenyl which is optionally monosubstituted to trisubstituted by identical or different substituents, suitable substituents being halogen, or alkyl, alkoxy or halogenoalkyl, each of which is straight-chain or branched and each of which has up to 4 carbon atoms and, in the case of halogenoalkyl, up to 9 identical or different halogen atoms. $R^{15}$ represents, in particular, methyl or ethyl, or phenyl which is optionally monosubstituted to trisubstituted by identical or different substituents from amongst fluorine, chlorine, methyl, methoxy and trifluoromethyl.

The iso(thio)cyanates of the formula (VI) are likewise generally known compounds of organic chemistry.

Formula (Ic) gives a general definition of the 5-amino-pyrazoles required as starting materials for carrying out preparation process (c). In this formula (Ic), $R^2$, $R^3$, $R^4$, $R^5$, $R^6$, $R^7$ and $R^8$ preferably represent those radicals which have already been mentioned in the description of the substances which can be used according to the invention, of the formula (I), as being preferred for these substituents. The 5-amino-pyrazoles of the formula (Ic) were hitherto unknown. They are obtained by preparation process (a) or (b).

Formula (VII) gives a general definition of the electrophilic agents furthermore required as starting materials for carrying out preparation process (c). In this formula (VII), $R^{1'}$ preferably represents chlorine, bromine, nitroso, nitro, hydroxysulphonyl or chlorosulphonyl, formyl, and straight-chain or branched alkyl or alkanoyl, each having up to 6 carbon atoms, or represents benzoyl which is optionally monosubstituted or polysubstituted by identical or different substituents, suitable substituents being halogen, in particular fluorine, chlorine or bromine, and alkyl, alkoxy or halogenoalkyl, each of which is straight-chain or branched and each of which has up to 4 carbon atoms and, in the case of halogenoalkyl, up to 9 identical or different halogen atoms, in particular methyl, methoxy or trifluoromethyl. E preferably represents halogen, in particular chlorine or bromine, hyroxyl, alkyl- or arylsulphonyloxy, alkanoyloxy or aroyloxy. Other electrophilic reagents which can be used are sulphuryl chloride, phosphorus oxychloride/dimethylformamide, nitrating acid and other substances customarily used for electrophilic substitutions. The electrophilic agents of the formula (VII), like the other customary electrophilic reagents, are generally known compounds. Formula (Id) gives a general definition of the 4-chlorosulphonyl-5-amino-pyrazoles required as starting materials for carrying out preparation process (d). In this formula (Id), $R^2$, $R^3$, $R^4$, $R^5$, $R^6$, $R^7$ and $R^8$ preferably represent those radicals which have already been mentioned in the description of the substances which can be used according to the invention, of the formula (I), as being preferred for these substituents. The 4-chlorosulphonyl-5-amino-pyrazoles were hitherto unknown. They are obtained by preparation process (c).

Formula (VIII) gives a general definition of the amines furthermore required as starting materials for carrying out preparation process (d). In this formula (VIII), $R^{16}$ and $R^{17}$ independently of one another preferably represent hydrogen or straight-chain or branched alkyl having up to 4 carbon atoms.

Formula (IX) gives a general definition of the alkali metal fluorides alternatively required as starting materials for carrying out preparation process (d). In this formula (IX), $M^\oplus$ preferably represents a sodium or potassium cation.

The amines of the formula (VIII), like the alkali metal fluorides of the formula (IX), are generally known compounds.

Formula (Ie) gives a general definition of the 4-acyl-5-amino-pyrazoles required as starting materials for carrying out preparation process (e). In this formula (Ie), $R^2$, $R^3$, $R^4$, $R^5$, $R^6$, $R^7$, $R^8$ and $R^{10}$ preferably represent those radicals which have already been mentioned in the description of the substances which can be used according to the invention of the formula (I) as being preferred for these substituents. The 4-acyl-5-amino-pyrazoles of the formula (Ie) were hitherto unknown. They are obtained by preparation process (c) or (f).

Formula (X) gives a general definition of the hydroxylamine derivatives furthermore required as starting materials for carrying out preparation process (e). In this formula (X), $R^{11}$ preferably represents those radicals which have already been mentioned in the description of the substances which can be used according to the invention, of the formula (I), as being preferred for these substituents. The hydroxylamine derivatives of the formula (X) and their hydrogen halide salts are generally known compounds.

Formula (XI) gives a general definition of the 4-cyano-5-amino-pyrazoles required as starting materials for carrying out preparation process (f). In this formula (XI), $R^2$, $R^3$, $R^4$, $R^5$, $R^6$, $R^7$ and $R^8$ preferably represent those radicals which have already been mentioned in the description of the substances which can be used according to the invention, of the formula (I), as being preferred for these substituents. Some of the 4-cyano-5-amino-pyrazoles of the formula (XI) are known (see, for example, European Pat. No. 26,034; European Pat. No. 34,945; European Pat. No. 53,687; DE-OS (German Published Specification) 3,226,496 and DE-OS (German Published Specification) 3,226,513) and some of them form the subject of (German Patent Application 3,337,543 of Oct. 15, 1983). They are obtained for example, in a manner analogous to preparation process (a), if phenylhydrazines of the formula (II)

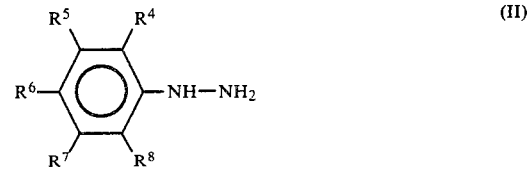
(II)

in which $R^4$, $R^5$, $R^7$ and $R^8$ have the meaning given above, are reacted with the known ethoxymethylenemalodinitriles of the formula (XII)

(XII)

if appropriate in the presence of a diluent, such as, for example, ethanol, and, if appropriate, in the presence of an acid-binding agent, such as, for example, sodium acetate, at temperatures of between $-20°$ C. and $+150°$ C.

Diluents which can be used for carrying out preparation process (a) and are suitable for both the first and the second reaction stage are inert organic solvents. Alcohols, such as methanol, ethanol, propanol, butanol, ethylene glycol or ethylene glycol monomethyl or ethyl ether are preferably used.

Suitable reaction auxiliaries for carrying out the first stage of preparation process (a) are organic or inorganic acids. Sulphuric acid or acetic acid, if appropriate also in the presence of a buffer substance, such as, for example, sodium acetate, are preferably used.

In carrying out the first stage of preparation process (a), the reaction temperatures can be varied within certain ranges. In general, the reaction is carried out at between $-30°$ and $+50°$ C., preferably between $-20°$ and $+20°$ C.

Suitable acid-binding agents for carrying out the second stage of preparation process (a) are all inorganic and organic bases which can customarily be used. Alkali metal carbonates or bicarbonates, such as sodium carbonate, potassium carbonate or potassium bicarbonate, are preferably used.

In carrying out the second stage of preparation process (a), the reaction temperatures can, as in the single-stage reaction procedure, be varied within a wide range. In general the reaction is carried out at between 0° C. and 200° C., preferably between 50° C. and $+150°$ C.

In carrying out preparation process (a), in general 1.0 to 3.0 mols, preferably 1.0 to 1.5 mols, of the acrylonitrile derivative of the formula (III) or (IIIa) or of 2,3-dichloropropionitrile of the formula (IIIb) are employed per mole of phenylhydrazine of the formula (II), both in the single-stage reaction procedure and in the two-stage reaction procedure, and, in the case of the two-stage process, if appropriate 1.0 to 10.0 mols of reaction auxiliary are employed in the first stage, and, if appropriate, 1.0 to 10.0 mols of acid-binding agent are employed in the second stage.

Working-up and isolation of the reaction products are carried out by customary methods, for example by removing the organic diluent, precipitating the reaction product in water, and filtering off the resulting product under suction and drying it.

Suitable diluents for carrying out preparation process (b) are likewise inert organic solvents. Preferably used compounds are aliphatic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran or ethylene glycol diethyl ether or ethylene glycol dimethyl ether, ketones, such as acetone, butanone, methyl isopropyl ketone or methyl isobutyl ketone, esters such as ethyl acetate, nitriles, such as acetonitrile or propionitrile, amides, such as dimethylformamide, dimethylacetamide, N-methylpyrrolidone or hexamethylphosphoric acid triamide. If acylating or alkylating agents of the formula (V) or (VI) are used in liquid form, it is also possible to employ these in an appropriate excess, as a diluent.

Suitable acid-binding agents for carrying out preparation process (b) are all inorganic and organic bases which can customarily be used. Preferably used compounds are alkali metal hydrides, hydroxides, amides, carbonates or bicarbonates, such as, for example, sodium hydride, sodium amide, sodium hydroxide, sodium carbonate or sodium bicarbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

In carrying out preparation process (b), the reaction temperatures can be varied within a wide range. In general, the reaction is carried out at between $-20°$ C. and $+150°$ C., preferably between $0°$ C. and $+100°$ C.

In carrying out preparation process (b), in general 1.0 to 20.0 mols, preferably 1.0 to 15.0 mols, of acylating or alkylating agent of the formula (V) or (VI) and, if appropriate, 1.0 to 3.0 mols, preferably 1.0 to 2.0 mols, of acid-binding agent are employed per mol of 5-amino-pyrazole of the formula (Ia). The reaction procedure and working-up and isolation of the reaction products of the formula (Ib) are carried out in a generally customary manner.

Suitable diluents for carrying out preparation process (c) are all solvents which can customarily be used for such electrophilic substitutions. Preferably, the acids or mixtures which constitute suitable reagents, such as, for example, sulphuric acid, chlorosulphonic acid, nitric acid, nitrating acid, sulfuryl chloride, phosphorus oxychloride/dimethylformamide or nitrating acid, are simultaneously used as diluents. Inert organic solvents, such as, for example, glacial acetic acid or chlorinated hydrocarbons, such as methylene chloride, chloroform or carbon tetrachloride, can, if necessary, also be used as diluents.

Suitable catalysts or reaction auxiliaries for carrying out preparation process (c) are likewise the catalysts customarily used for such reactions; acidic catalysts, such as, for example, sulphuric acid, iron(III) chloride or other Lewis acids or acetic anhydride, are preferably used.

In carrying out preparation process (c), the reaction temperatures can be varied within a relatively wide range. In general, the reaction is carried out at between $-50°$ C. and $+200°$ C., preferably between $-20°$ C. and $+150°$ C.

In carrying out preparation process (c), in general 1.0 to 10.0 mols, preferably 1.0 to 5.0 mols, of the electrophilic agent of the formula (VII) and, if appropriate, 0.1 to 10 mols of catalyst or reaction auxiliary are employed per mol of 5-amino-pyrazole of the formula (Ic). The reaction procedure and working-up and isolation of the reaction products of formula (I) are carried out in a generally customary manner.

Suitable diluents for carrying out preparation process (d) are likewise inert organic solvents. The solvents mentioned in the case of preparation process (b) are preferably used. For the reaction with an alkali metal fluoride of the formula (IX), it is also possible to use water or aqueous mixtures with one of the solvents mentioned in the case of process (b).

Suitable acid-binding agents for carrying out preparation process (d) are likewise all organic or inorganic bases which can customarily be used. Alkali metal hydroxides, carbonates or bicarbonates, such as, for example, potassium carbonate or sodium bicarbonate, are preferably used. Tertiary organic bases, such as triethylamine or pyridine, are also suitable.

In preparation process (d), the reaction temperatures can likewise be varied within a wide range. In general, the reaction is carried out at between $-20°$ C. and $+120°$ C., preferably between $0°$ C. and $+90°$ C.

In carrying out preparation process (d), in general 1.0 to 3.0 mols, preferably 1.0 to 2.0 mols, of the amine of the formula (VIII) or the alkali metal fluoride of the formula (IX) and, if appropriate, 1.0 to 3.0 mols, preferably 1.0 to 2.0 mols, of acid-binding agent are employed per mol of 4-chlorosulphonyl-5-amino-pyrazole of the formula (Id). The reaction procedure and working-up and isolation of the reaction products of the formula (I) are carried out in a customary manner.

Suitable diluents for carrying out preparation process (e) are likewise inert organic solvents. Alcohols, such as, for example, methanol, ethanol or propanol, are preferably used.

Suitable acid-binding agents for carrying out preparation process (e) are likewise all organic and inorganic bases which can customarily be used. The acid-binding agents mentioned in the case of process (b) are preferably used.

In carrying out preparation process (e), the reaction temperature can likewise be varied within a wide range. In general, the reaction is carried out at between $+20°$ C. and $+150°$ C., preferably between $+20°$ C. and $+120°$ C.

In carrying out preparation process (e), in general 1.0 to 3.0 mols, preferably 1.0 to 2.0 mols, of the hydroxylamine derivatives of the formula (X) and, if appropriate, 1.0 to 3.0 mols of acid-binding agent are employed per mol of the 4-acyl-5-amino-pyrazole of the formula (Ie). The reaction procedure and working-up and isolation of the reaction products of the formula (I) are carried out in a generally customary manner.

Suitable diluents for carrying out preparation process (f) are inert organic solvents or aqueous systems. The formic acid used as a reactant is preferably used as the diluent, in an appropriate excess and, if required, as a mixture with water.

In carrying out preparation process (f), the reaction temperatures can likewise be varied within a wide range. In general, the reaction is carried out at between $0°$ C. and $+150°$ C., preferably between $+20°$ C. and $130°$ C.

In carrying out preparation process (f), in general 0.1 to 3 mols, preferably 0.5 to 2 mols, of Raney nickel and in general 10 to 30 mols, preferably 1.0 to 15 mols, of formic acid are employed per mol of 4-cyano-5-aminopyrazole of the formula (XI).

The reaction procedure and working-up and isolation of the reaction products of the formula (I) are carried out in a customary manner analogous to known methods (see, for example, Chem. Pharm. Bull. 24, 3129 [1976]).

The active compounds which can be employed according to the invention can be used as defoliants, desiccants and agents for destroying broad-leaved plants, and especially as weedkillers. By weeds, in the broadest sense, there are to be undersood all plants which grow in locations where they are undesired. Whether the substances which can be used according to the invention act as total or selective herbicides depends essentially on the amount used.

The active compounds which can be employed according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds which can be employed according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

In addition to exhibiting a particularly good general herbicidal activity, the active compounds of the formula (I) which can be used according to the invention also exhibit substantially improved selectivity with regard to crop plants in important cultures, and can be employed as agents for selectively combating weeds both in dicotyledon cultures, such as, for example, cotton plantings, soy beans or groundnuts, and in monocotyledon cultures, in particular cereals, such as, for example, wheat.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylene or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds which can be employed according to the invention, as such or in the form of their formulations, can also be used, for combating weeds, as mixtures with known herbicides, finished formulations or tank mixtures being possible.

Suitable herbicides for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals, 4-amino-3-methyl-6-phenyl-1,2,4-triazin-5(4H)-one for combating weeds in sugarbeet and 4-amino-6-(1,1-dimethylethyl)-3-methylthio-1,2,4-triazin-5(4H)-one for combating weeds in soy beans. Mixtures with N,N-dimethyl-N'-(3-trifluoromethylphenyl)-urea, N,N-dimethyl-N'-(3-chloro-4-methylphenyl)-urea, N,N-dimethyl-N'-(4-isopropylphenyl)-urea, 4-amino-6-t-butyl-3-ethylthio-1,2,4-triazin-5(4H)-one, 2,4-dichlorophenoxyacetic acid, 2,4-dichlorophenoxypropionic acid, (2-methyl-4-chlorophenoxy)-acetic acid, (4-chloro-2-methyl-phenoxy)-propionic acid, chloroacetic acid N-(methoxymethyl)-2,6-dimethylanilide, 2-ethyl-6-methyl-N-(1-methyl-2-methoxyethyl)-chloroacetanilide, 2,6-dinitro-4-trifluoromethyl-N,N-dipropylaniline, and 2-benzyloxyethyl, trimethylsilylmethyl or 2,2-diethoxyethyl 2-[4-(3,5-dichloropyrid-2-yloxy)-phenoxy]-propionate are also possible. Surprisingly, some mixtures also exhibit a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds which can be used according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg of active compound per hectare of soil area, preferably between 0.01 and 5 kg per ha.

The examples which follow illustrate the preparation and the use of the active compounds which can be used according to the invention.

PREPARATION EXAMPLES

Example 1

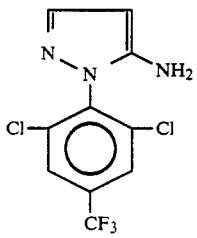

Process a 20 mg of disodium ethylenediamine-tetraacetate (=Titriplex III) in 150 ml of methanol are added dropwise to 24.5 g (0.1 mol) of 2,6-dichloro-4-trifluoromethylphenylhydrazine at the reflux temperature, and 25 ml (27.6 g/0.3 mol) of 2-chloroacrylonitrile are added. When the addition is complete, heating is continued for a further 8 hours at the reflux temperature, after which 9 ml (0.16 mol) of 96% strength sulphuric acid are added dropwise and heating is continued for a further 6 hours at the reflux temperature. 33.5 g (0.3 mol) of anhydrous sodium carbonate are added to the cooled reaction mixture. After 4 hours, the solvent is removed in vacuo, the residue is taken up in 500 ml of water, and the solution is stirred for 10 hours at room temperature. The precipitate which separates out is filtered off, rinsed with water and dried in vacuo at 50° C.

28.5 g (96% of theory) of 5-amino-1-(2,6-dichloro-4-trifluoromethylphenyl)-pyrazole of melting point 103°–105° C. are obtained.

Example 2

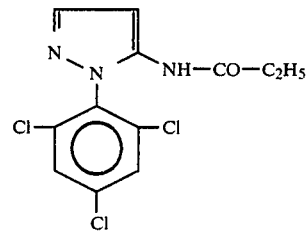

Process b 5 ml (5.3 g/0.05 mol) of 98% strength propionyl chloride and then 5 ml (5.0 g/0.063 mol) of anhydrous pyridine are added in succession to 13.2 g (0.05 mol) of 5-amino-1-(2,4,6-trichlorophenyl)-pyrazole in 100 ml of dichloromethane at room temperature, while stirring. During the addition, the temperature increases to 40° C. When the addition is complete, stirring is continued for a further 16 hours at room temperature, 50 ml of dichloromethane are added, the mixture is washed with twice 100 ml of water, 100 ml of saturated sodium bicarbonate solution and 100 ml of sodium chloride solution and is dried over magnesium sulphate, and the solvent is removed in vacuo. The solid residue is washed with a small amount of hexane and is dried.

12.5 g (81% of theory) of 5-propionamido-1-(2,4,6-trichlorophenyl)-pyrazole of melting point 125° C. are obtained.

Example 3

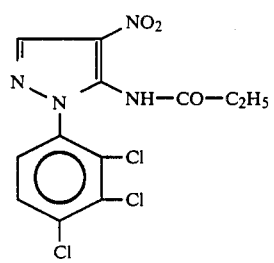

Process c 2 ml (2.17 g/0.021 mol) of acetic anhydride and then 0.9 ml (1.3 g/0.02 mol) of 98% strength nitric acid are added in succession to 6.4 g (0.02 mol) of 5-propionamido-1-(2,3,4-trichlorophenyl)-pyrazole in 20 ml of glacial acetic acid at 10° C. When the addition is complete, the mixture is stirred for 16 hours at 25° C. To work up the mixture, it is evaporated down in vacuo, the residue is taken up in 20 ml of diethyl ether, the solution is washed three times with a total of 50 to 100 ml of concentrated sodium bicarbonate solution and twice with 50 ml of saturated sodium chloride solution, the solvent is removed in a vacuum from a water pump, and the solid residue is washed with a small amount of water and dried in a high vacuum at 30° C. to 40° C. 5.5 g (76% of theory) of 4-nitro-5-propionamido-1-(2,3,4-trichlorophenyl)-pyrazole of melting point 79°–81° C. are obtained.

Example 4

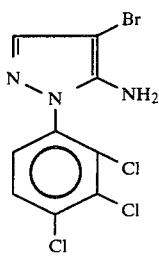

Process c

A solution of 1.6 g (0.02 mol) of bromine in 5 ml of glacial acetic acid is added dropwise to 2.6 g (0.01 mol) of 5-amino-1-(2,3,4-trichlorophenyl)-pyrazole in 10 ml of glacial acetic acid at 20° C., while stirring. When the addition is complete, stirring is continued for a further 3 hours at 20° C., after which 30 ml of water and 3 g (0.022 mol) of sodium acetate trihydrate are added, stirring is continued for a further hour, and the crystalline precipitate is filtered off under suction, washed with water and dried at 50° C. to 60° C. in vacuo. 3.2 g (94% of theory) of 5-amino-4-bromo-1-(2,3,6-trichlorophenyl)-pyrazole of melting point 129° C. are obtained.

Example 5

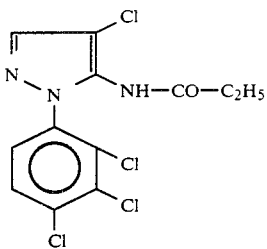

Process c 1.2 g (0.009 mol) of sulfuryl chloride are added dropwise to 2.7 g (0.0085 mol) of 5-propionamide-1-(2,3,4-trichlorophenyl)-pyrazole in 20 ml of dichloromethane at 0° C. to 5° C. When the addition is complete, stirring is continued for a further 16 hours at room temperature, the mixture is diluted with 30 ml of dichloromethane, washed several times with water, saturated sodium bicarbonate solution and saturated sodium chloride solution, dried over sodium sulphate and evaporated down in vacuo, and the residue is dried at 50° C. in a high vacuum. 2.5 g (83% of theory) of 4-chloro-5-propionamido-1-(2,3,4-trichlorophenyl)-pyrazole of melting point 122° C. are obtained.

Example 6

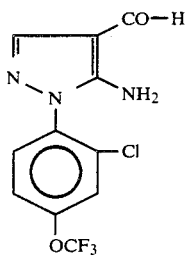

Process f 12 g (0.042 mol) of 5-amino-4-cyano-1-(2-chloro-4-trifluoromethoxy-phenyl)-pyrazole are boiled under reflux with 5 g of Raney nickel in 50 ml of 75% strength aqueous formic acid for 1 hour; the still warm solution is filtered under suction, the residue is rinsed with water, the filtrate is extracted several times with ether, and the combined ether phases are washed with saturated sodium bicarbonate solution, dried over sodium sulphate and evaporated down in vacuo. 8.0 g (62% of theory) of 5-amino-1-(2-chloro-4-trifluoromethoxyphenyl)-4-formyl-pyrazole are obtained in the form of an oil.

$^1$H-NMR δ[ppm]=5.7 (s,2H)—singlet, 7.3–7.6 (m,3H)—multiplet, 7.85 (s,1H)—singlet, 9.6 (s,1H)—singlet.

Example 7

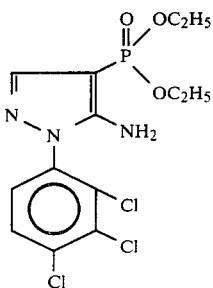

Process a 6.3 g (0.03 mol) of 2,3,4-trichlorophenylhydrazine, 5.8 g (0.025 mol) of ethoxymethylene-diethylphosphonoacetonitrile and 1 g of (0.012 mol) of anhydrous sodium acetate are suspended in 10 ml of glacial acetic acid, and the suspension is stirred for 48 hours at room temperature. 50 ml of dichloromethane and 100 ml of water are added to the reaction mixture. The organic phase is separated off and washed once in each case with 50 ml of saturated sodium bicarbonate solution and 30 ml of saturated sodium chloride solution. After the solution has been dried over magnesium sulphate, the solvent is distilled off in vacuo, the oily residue is dissolved in 15 ml of ethoxyethanol, and the solution is heated under reflux for 5 hours. It is then cooled to room temperature, 30 ml of water are added to the solution and stirring is continued until the initially oily precipitate crystallizes. The slightly yellow crystals are filtered off under suction, washed with water and dried in vacuo at 50°–60° C.

5.6 g (46.8% of theory) of 5-amino-4-diethylphosphono-1-(2,3,4-trichlorophenyl)-pyrazole of melting point 114° C. are obtained.

PREPARATION OF THE STARTING COMPOUND

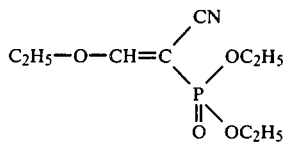

35.4 g (0.2 mol) of diethylphosphonoacetonitrile (see Houben-Weyl "Methoden der organischen Chemie" (Methods of organic chemistry), Volume E2, page 345, 4th Edition, Thieme Verlag Stuttgart, 1982), 42 ml (0.45 mol) of acetic anhydride and 56 ml (0.34 mol) of triethyl o-formate are stirred for 2 hours at 110° C. Thereafter, the low-boiling compounds are distilled off over a short column under atmospheric pressure, the bottom temperature increasing to 140° C. This temperature is maintained for a further 4 hours, and the unreacted starting compounds are then distilled off, first under a vacuum from a water pump and then under a vacuum from an oil pump. 20.5 g (44% of theory) of ethoxymethylene-diethylphosphonoacetonitrile remain as an oil at the bottom.

$^1$H-NMR (CDCl$_3$)=$\delta$=7.63 ppm (d,1H)—doublet, 4.32 ppm (q,2H)—quartet, 4.15 ppm (m,4H)—multiplet, 1.45–1.35 ppm (m,9H)—multiplet.

The following compounds of the general formula (I) are obtained in a corresponding manner and in accordance with the general preparation data.

TABLE 2

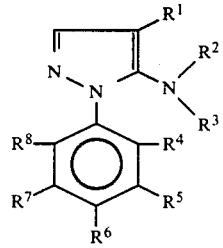

(I)

| Example No. | R$^1$ | R$^2$ | R$^3$ | R$^4$ | R$^5$ | R$^6$ | R$^7$ | R$^8$ | Melting point (°C.) |
|---|---|---|---|---|---|---|---|---|---|
| 8 | NO$_2$ | C$_2$H$_5$CO | H | Cl | H | Cl | H | Cl | 54° C. |
| 9 | NO$_2$ | C$_2$H$_5$CO | H | Cl | H | CF$_3$ | H | Cl | 48° C. |
| 10 | NO$_2$ | C$_2$H$_5$CO | H | Cl | H | CF$_3$ | H | H | 115° C. (decomposition) |
| 11 | NO$_2$ | C$_2$H$_5$CO | H | Cl | H | SCF$_3$ | H | Cl | 96–99° C. |
| 12 | NO$_2$ | C$_2$H$_5$CO | H | Cl | H | OCF$_3$ | H | H | 65° C. |
| 13 | NO$_2$ | C$_2$H$_5$CO | H | Cl | Cl | CF$_3$ | Cl | Cl | 54–60° C. |
| 14 | NO$_2$ | C$_2$H$_5$CO | H | CF$_3$ | H | Cl | H | H | |
| 15 | NO$_2$ | H | H | Cl | H | Cl | H | Cl | 218° C. |
| 16 | NO$_2$ | CH$_3$CO | H | Cl | H | CF$_3$ | H | Cl | 50° C. |
| 17 | NO$_2$ | CH$_3$CO | H | Cl | H | SCF$_3$ | H | Cl | 58–61° C. |
| 18 | NO$_2$ | CH$_3$(CH$_2$)$_2$CO | H | Cl | H | CF$_3$ | H | Cl | 44° C. |
| 19 | NO$_2$ | CH$_3$OCO | H | Cl | H | CF$_3$ | H | Cl | 141–43° C. |
| 20 | NO$_2$ | ClCH$_2$CO | H | Cl | H | CF$_3$ | H | Cl | 130–33° C. |
| 21 | NO$_2$ | C$_2$H$_5$CO | H | Cl | H | Cl | H | H | 63° C. |
| 22 | H | H | H | Cl | H | Cl | H | Cl | 113° C. |
| 23 | H | H | H | Cl | H | CF$_3$ | H | H | 88–92° C. |
| 24 | H | H | H | Cl | H | SCF$_3$ | H | Cl | 79° C. |
| 25 | H | H | H | Cl | Cl | Cl | H | H | 152° C. |
| 26 | H | H | H | Cl | Cl | CF$_3$ | Cl | Cl | 103–10° C. |
| 27 | H | H | H | Cl | H | OCF$_3$ | H | H | 73–76° C. |
| 28 | H | C$_2$H$_5$CO | H | Cl | Cl | Cl | H | H | 55° C. |
| 29 | H | C$_2$H$_5$CO | H | Cl | H | CF$_3$ | H | H | 106–10° C. |
| 30 | H | C$_2$H$_5$CO | H | Cl | H | SCF$_3$ | H | Cl | 136° C. |
| 31 | H | C$_2$H$_5$CO | H | Cl | H | CF$_3$ | H | Cl | 146° C. |
| 32 | H | C$_2$H$_5$CO | H | Cl | H | OCF$_3$ | H | H | Oil |
| 33 | H | C$_2$H$_5$CO | H | Cl | Cl | CF$_3$ | Cl | Cl | 154–58° C. |
| 34 | H | C$_2$H$_5$CO | H | CF$_3$ | H | Cl | H | H | Oil |
| 35 | H | C$_2$H$_5$CO | H | Cl | H | Cl | H | H | Oil |
| 36 | H | C$_2$H$_5$CO | H | Cl | H | SO$_2$CF$_2$Cl | H | Cl | 134° C. |
| 37 | H | CH$_3$CO | C$_2$H$_5$CO | Cl | Cl | Cl | H | H | 142° C. |
| 38 | H | CH$_3$CO | CH$_3$CO | Cl | Cl | Cl | H | H | 142° C. |
| 39 | H | CH$_3$OCO | H | Cl | H | CF$_3$ | H | Cl | 123–126° C. |
| 40 | H | CH$_3$CO | H | Cl | H | CF$_3$ | H | Cl | 173–76° C. |
| 41 | H | CH$_3$CO | H | Cl | H | SCF$_3$ | H | Cl | 131° C. |
| 42 | H | CH$_3$(CH$_2$)$_2$CO | H | Cl | H | CF$_3$ | H | Cl | 128–31° C. |
| 43 | H | ClCH$_2$CO | H | Cl | H | CF$_3$ | H | Cl | 149–50° C. |
| 44 | Br | C$_2$H$_5$CO | H | Cl | Cl | Cl | H | H | 78° C. |
| 45 | I | H | H | Cl | Cl | Cl | H | H | 162° C. |
| 46 | CH$_3$O\|N=CH— | H | H | Cl | Cl | Cl | H | H | 156–59° C. |
| 47 | HON=CH— | H | H | Cl | H | OCF$_3$ | H | H | 180° C. |

TABLE 2-continued

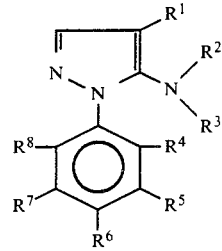

(I)

| Example No. | R¹ | R² | R³ | R⁴ | R⁵ | R⁶ | R⁷ | R⁸ | Melting point (°C.) |
|---|---|---|---|---|---|---|---|---|---|
| 48 | $(C_2H_5O)_2P(O)-$ | $C_2H_5CO$ | H | Cl | Cl | Cl | H | H | Oil |
| 49 | $NO_2$ | $C_2H_5CO$ | H | Cl | H | $SO_2CCl_2F$ | H | Cl | 156–58° C. |
| 50 | $NO_2$ | H | H | Cl | H | $CF_3$ | H | Cl | 189–90° C. |
| 51 | $NO_2$ | H | H | Cl | H | $SO_2CCl_2F$ | H | Cl | 208–09° C. |
| 52 | H | $C_2H_5CO$ | $CH_3$ | Cl | H | Cl | H | Cl | 150–51 |
| 53 | $NO_2$ | $C_2H_5CO$ | $CH_3$ | Cl | H | Cl | H | Cl | 192–98 |
| 54 | H | $C_2H_5CO$ | H | Cl | H | $SCF_3$ | H | H | Oil |
| 55 | H | △-CO | H | Cl | H | $CF_3$ | H | Cl | 69–71 |
| 56 | H | $C_{11}H_{23}CO$ | H | Cl | H | $CF_3$ | H | Cl | 63–66 |
| 57 | $SCCl_2F$ | H | H | Cl | H | H | Cl | | 102 |
| 58 | $SCCl_2F$ | $C_2H_5CO$ | H | Cl | H | Cl | H | Cl | 128–29 |
| 59 | $NO_2$ | H | H | Cl | H | $OCF_3$ | H | H | 50 |
| 60 | $NO_2$ | △-CO | H | Cl | H | $CF_3$ | H | Cl | 165–68 |
| 61 | $NO_2$ | $C_{11}H_{23}CO$ | H | Cl | H | $CF_3$ | H | Cl | 60–70 |
| 62 | $NO_2$ | $C_2H_5CO$ | H | Cl | H | $SCF_3$ | H | H | 90–93 |
| 63 | Cl | $C_2H_5CO$ | H | Cl | H | $CF_3$ | H | Cl | 63–65 |
| 64 | H | $C_2H_5CO$ | H | Cl | H | $OCF_3$ | H | Cl | 50–56 |
| 65 | $SOCCl_2F$ | $C_2H_5CO$ | H | Cl | H | Cl | H | Cl | 143–46 |
| 66 | $NO_2$ | $C_2H_5CO$ | H | Cl | H | $SO_2CF_3$ | H | H | 60–64 |
| 67 | $SO_2CCl_2F$ | $C_2H_5CO$ | H | Cl | H | Cl | H | Cl | 136–39 |
| 68 | H | $C_2H_5CO$ | H | Cl | Cl | $CF_3$ | H | Cl | 129–32 |
| 69 | NO | H | H | Cl | H | $CF_3$ | H | Cl | 227 |
| 70 | $NO_2$ | H | H | Cl | H | $SO_2CF_3$ | H | H | 68–70 |
| 71 | $NO_2$ | $C_2H_5CO$ | H | Cl | H | $OCF_3$ | H | Cl | 130–35 |
| 72 | $NO_2$ | $C_2H_5CO$ | H | Cl | H | $SO_2CF_3$ | H | Cl | 132–34 |
| 73 | $NO_2$ | $C_2H_5CO$ | H | Cl | Cl | $CF_3$ | H | Cl | 50–52 |
| 74 | $(C_2H_5O)_2P(O)$ | H | H | Cl | H | $CF_3$ | H | Cl | Oil |
| 75 | $NO_2$ | H | H | Cl | H | $SCF_3$ | H | H | 56–60 |
| 76 | $NO_2$ | H | H | Cl | $SCF_3$ | H | Cl | | 145–49 |
| 77 | $NO_2$ | H | H | Cl | $OCH_3$ | | Cl | | 206–08 |
| 78 | $NO_2$ | H | H | Cl | H | $SO_2CF_3$ | H | Cl | 249–53 |
| 79 | $NO_2$ | H | H | Cl | Cl | $CF_3$ | H | Cl | 78–85 |
| 80 | H | $CH_3NHCO$ | H | Cl | H | $CF_3$ | H | Cl | 178–82 |
| 81 | H | Ph-O-CO | H | Cl | H | $CF_3$ | H | Cl | 65–67 |
| 82 | H | $(CH_3)_2NCO$ | H | Cl | H | $CF_3$ | H | Cl | 137–38 |
| 83 | H | $C_2H_5CO$ | H | Cl | Cl | Cl | H | Cl | 62–67 |
| 84 | $NO_2$ | $C_2H_5CO$ | H | Cl | Cl | Cl | H | Cl | 60–67 |
| 85 | H | $ClCH_2CH_2-CO$ | H | Cl | H | $CF_3$ | H | Cl | 120–24 |
| 86 | $NO_2$ | $CH_3NHCO$ | H | Cl | H | $CF_3$ | H | Cl | 212–14 |
| 87 | $NO_2$ | Ph-O-CO | H | Cl | H | $CF_3$ | H | Cl | 48–52 |
| 88 | $NO_2$ | H | H | Cl | Cl | Cl | H | Cl | 83–89 |
| 89 | $NO_2$ | H | $CH_3$ | Cl | H | Cl | H | Cl | 167–75 |
| 90 | H | H | $CH_3$ | Cl | H | Cl | H | Cl | 186–88 |

TABLE 2-continued

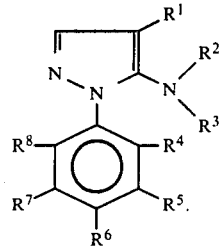
(I)

| Example No. | R¹ | R² | R³ | R⁴ | R⁵ | R⁶ | R⁷ | R⁸ | Melting point (°C.) |
|---|---|---|---|---|---|---|---|---|---|
| 91 | H | ClCH₂—CO | H | Cl | H | CF₃ | H | H | 103–05 |
| 92 | H | ClCH₂—CO | H | Cl | H | OCF₃ | H | H | 84–87 |
| 93 | NO₂ | H | H | Cl | H | CF₃ | H | H | 55–58 |
| 94 | NO₂ | ClCH₂CH₂—CO | H | Cl | H | CF₃ | H | Cl | 135–40 |
| 95 | NO₂ | ClCH₂—CO | H | Cl | H | OCF₃ | H | H | Oil |
| 96 | NO₂ | ClCH₂—CO | H | Cl | H | CF₃ | H | H | 111–13 |
| 97 | H | C₂H₅CO | H | Cl | F | CF₃ | F | Cl | 121–23 |
| 98 | NO₂ | C₂H₅CO | H | Cl | F | CF₃ | F | Cl | 135–37 |
| 99 | H | C₂H₅CO | H | Cl | F | Cl | F | Cl | 190–93 |
| 100 | NO₂ | H | CH₃ | Cl | H | CF₃ | H | H | 120–23 |
| 101 | NO₂ | C₂H₅CO | CH₃ | Cl | H | CF₃ | H | Cl | 140–54 |
| 102 | NO₂ | H | H | Cl | F | CF₃ | F | Cl | 158–65 |
| 103 | NO₂ | C₂H₅CO | H | Cl | F | Cl | F | Cl | 130–33 |
| 104 | NO₂ | CH₂=CH—CO | H | Cl | H | CF₃ | H | Cl | 55–65 |
| 105 | NO₂ | H | H | Cl | F | Cl | F | Cl | 210–20 |
| 106 | H | HCO | H | Cl | H | CF₃ | H | Cl | 144–50 |
| 107 | NO₂ | C₂H₅CO | H | Cl | H | OCH₃ | H | Cl | 165–74 |
| 108 | NO₂ | HCO | H | Cl | H | CF₃ | H | Cl | 144–50 |
| 109 | NO₂ | H | CH₃ | Cl | H | CF₃ | H | Cl | 120–40 |
| 110 | SCCl₂F | H | H | Cl | H | CF₃ | H | Cl | 99–105 |
| 111 | SOCCl₂F | H | H | Cl | H | CF₃ | H | Cl | 55–62 |
| 112 | H | CH₃CO | H | Cl | Cl | CF₃ | H | Cl | 158–62 |
| 113 | SO₂CCl₂F | H | H | Cl | H | CF₃ | H | Cl | 135–38 |
| 114 | NO₂ | CH₃CO | H | Cl | Cl | CF₃ | H | Cl | 124–33 |
| 115 | H | CH₃CO | H | Cl | H | CF₃ | H | H | 50–52 |
| 116 | NO₂ | CH₃CO | H | Cl | H | CF₃ | H | H | 62–65 |
| 117 | H | H | CH₃ | Cl | H | CF₃ | H | Cl | 135–37 |
| 118 | H | ⌬—CO (phenyl-CO) | H | Cl | H | CF₃ | H | Cl | 62–64 |
| 119 | NO₂ | ClCH₂CH₂CH₂CO | H | Cl | H | CF₃ | H | Cl | 60–63 |
| 120 | NO₂ | ⌬—CO (phenyl-CO) | H | Cl | H | CF₃ | H | Cl | 157–65 |
| 121 | H | C₂H₅CO | H | Cl | H | Br | H | H | 86–88 |
| 122 | H | H | H | Br | H | Br | H | Br | 141–43 |
| 123 | H | C₂H₅CO | H | Br | H | Br | H | Br | 147–50 |
| 124 | H | H | H | Cl | H | Br | H | Cl | 102 |
| 125 | H | H | H | Br | H | Cl | H | Br | 98 |
| 126 | NO₂ | H | H | Cl | H | Br | H | H | 95–98 |
| 127 | H | H | H | I | H | I | H | H | 138–40 |
| 128 | NO₂ | C₂H₅CO | H | Br | H | Br | H | Br | 92–94 |
| 129 | H | C₂H₅CO | H | Br | H | Cl | H | Br | 138–40 |
| 130 | H | C₂H₅CO | H | Cl | H | Br | H | Cl | 142–48 |
| 131 | H | H | H | Br | H | Cl | H | Cl | 105–07 |
| 132 | NO₂ | C₂H₅CO | H | Br | H | Cl | H | Br | 146–48 |
| 133 | H | ClCH₂CO | H | Br | H | Cl | H | Br | 127–30 |
| 134 | H | H | H | Br | H | F | H | H | 58–60 |
| 135 | NO₂ | H | H | Br | H | Cl | H | Br | 230 |
| 136 | H | H | H | Br | Cl | Cl | H | Br | 120–25 |
| 137 | NO₂ | C₂H₅CO | H | Cl | H | Br | H | Cl | 94 |
| 138 | NO₂ | H | H | Cl | H | Br | H | Cl | 198 |
| 139 | H | C₂H₅CO | H | Br | H | Br | H | Cl | 114–18 |
| 140 | NO₂ | ClCH₂CO | H | Br | H | Cl | H | Br | 115–20 |
| 141 | H | C₂H₅CO | H | I | H | I | H | H | Oil |
| 142 | H | H | H | Br | Cl | Br | H | Cl | 170 |
| 143 | NO₂ | C₂H₅CO | H | Br | H | Br | H | Cl | 89–93 |
| 144 | NO₂ | H | H | Br | H | Br | H | Cl | 208–10 |
| 145 | H | C₂H₅CO | H | Br | Cl | Cl | H | Br | 165 |

TABLE 2-continued

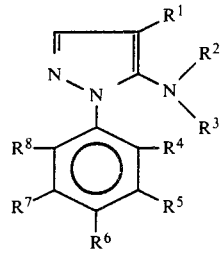

| Example No. | $R^1$ | $R^2$ | $R^3$ | $R^4$ | $R^5$ | $R^6$ | $R^7$ | $R^8$ | Melting point (°C.) |
|---|---|---|---|---|---|---|---|---|---|
| 146 | H | $C_2H_5CO$ | H | Br | Cl | Br | H | Cl | 140-50 |
| 147 | $NO_2$ | $C_2H_5CO$ | H | I | H | I | H | H | 55-60 |
| 148 | $NO_2$ | $C_2H_5CO$ | H | Br | Cl | Cl | H | Br | 130-40 |
| 149 | $NO_2$ | $C_2H_5CO$ | H | Br | H | F | H | H | 72-74 |
| 150 | $NO_2$ | $C_2H_5CO$ | H | Br | H | $OCF_3$ | H | H | 83-85 |
| 151 | Br | H | H | Cl | H | Cl | H | Cl | 119 |
| 152 | $SCH_3$ | H | H | Cl | H | Cl | H | Cl | 114 |
| 153 | Br | H | H | $OCH_3$ | H | Cl | H | Cl | 67-70 |
| 154 | $SCH_3$ | $C_2H_5CO$ | H | Cl | H | Cl | H | Cl | 92-95 |
| 155 | $SO_2CH_3$ | $C_2H_5CO$ | H | Cl | H | Cl | H | Cl | 146-50 |
| 156 | —CHO | H | H | Cl | H | $OCF_3$ | H | H | Oil |
| 157 | —CHO | $C_2H_5CO$ | H | Cl | H | $OCF_3$ | H | H | Oil |
| 158 | —CH=$NOCH_3$ | H | H | Cl | H | $OCF_3$ | H | H | 138-39 |
| 159 | H | $ClCH_2CH_2CH_2CO$ | H | Cl | H | $CF_3$ | H | Cl | Oil |

USE EXAMPLES

The compound listed below is used as a comparative substance in the use examples which follow:

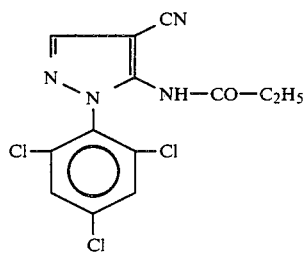

4-Cyano-5-propionamido-1-(2,4,6-trichlorophenyl)-pyrazole (disclosed in U.S. Pat. No. 4,459,150 and U.S. Pat. No. 4,496,390).

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example, the compound according to preparation Example 3 is clearly superior to the prior art, both in herbicidal activity and in selectivity with respect to crop plants.

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, for example, the compound according to preparation Example 3 is clearly superior to the prior art, both in herbicidal activity and in selectivity with respect to crop plants.

It will be understood that the specification and examples are illustrative but not limitative of the present invention and that other embodiments within the spirit and scope of the invention will suggest themselves to those skilled in the art.

We claim:

1. A method of combating unwanted vegetation which comprises applying to such vegetation or to a locus from which it is desired to exclude such vegetation a herbicidally effective amount of a 5-amino-1-phenyl-pyrazole of the formula

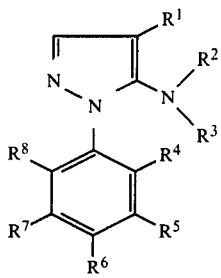

in which
- $R^1$ represent hydrogen, nitroso, nitro, halogen, $C_{1-6}$ alkyl, $C_{1-6}$ halogenoalkyl with up to 9 halogen atoms, or represents unsubstituted phenyl or phenyl substituted by halogen, nitro, alkyl, alkoxy, and/or halogenoalkyl, each having up to 4 carbon atoms, or represents one of the radicals —S(O)$_n$—$R^9$;

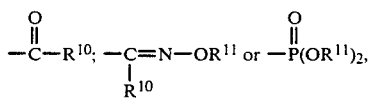

- $R^2$ represents hydrogen or a radical

- $R^3$ independently or $R^2$ represents the same radicals as $R^2$ and additionally represents alkyl having up to 4 carbon atoms,
- $R^4$ and $R^6$ independently of one another represent cyano, nitro, halogen, alkyl, alkoxy, alkoxy carbonyl, each of which has up to 4 carbon atoms and furthermore represents halogenoalkyl or halogenoalkoxy, each of which has up to 4 carbon atoms and up to 9 halogen atoms or represents a radical —S(O)$_n$—$R^{13}$, and
- $R^5$, $R^7$ and $R^8$ independently of one another and of $R^4$ and $R^6$ represent the same radicals as $R^4$ and $R^6$ and additionally represent hydrogen, and
- $R^9$ represents hydrogen, hydroxyl, amino, fluorine, chlorine, bromine, alkylamino, dialkylamino, alkyl, halogenoalkyl, each of which has up to 4 carbon atoms in the individual alkyl parts, and said halogenoalkyl having up to 9 halogen atoms and $R^9$ also represents unsubstituted phenyl or phenyl substituted by halogen, alkyl, alkoxy and/or halogenoalkyl, each of which has up to 4 carbon atoms, and said halogenoalkyl having up to 9 halogen atoms,
- $R^{10}$ represents hydrogen, alkyl having up to 4 carbon atoms, or unsubstituted phenyl or phenyl substituted by halogen, alkyl, alkoxy and or halogenoalkyl, each of which has up to 4 carbon atoms, said halogenoalkyl having up to 9 halogen atoms,
- $R^{11}$ represents hydrogen, alkyl alkenyl or alkinyl, each of which has up to 8 carbon atoms, halogenoalkyl having up to 4 carbon atoms and up to 6 halogen atoms and phenylalkyl having up to 4 carbon atoms in the alkyl part,
- $R^{12}$ represents hydrogen, alkyl which has 1 to 12 carbon atoms, alkenyl, alkinyl, alkoxyalkyl, alkylthioalkyl, alkoxy, alkylthio, alkylamino, dialkylamino or halogenoalkyl, each of which has up to 4 carbon atoms in the individual alkyl parts, said halogenoalkyl having up to 9 halogen atoms and furthermore represents unsubstituted cycloalkyl which has 3 to 7 carbon atoms or cycloalkyl substituted by halogen, lower alkyl and/or lower halogenoalkyl, or represents phenyl, phenoxy, phenylthio or phenylamino, each of which is unsubstituted or substituted by halogen, alkyl, alkoxy and/or halogenoalkyl, each of which has up to 4 carbon atoms, and the halogenoalkyl having up to 9 halogen atoms,
- $R^{13}$ represents amino, alkyl, halogenoalkyl, alkylamino or dialkylamino, each of which has up to 4 carbon atoms in the individual alkyl parts and, the halogenoalkyl having up to 9 halogen atoms,
- X represents oxygen or sulphur, and
- n represents the numbers 0, 1 or 2.

2. The method according to claim 1, in which
- $R^1$ represents hydrogen, nitroso, nitro, fluorine, chlorine, bromine, methyl, ethyl, n- and i-propyl, n-, i, s- and t-butyl, trifluoromethyl, or phenyl which is optionally monosubstituted to trisubstituted by identical or different substituents from amongst fluorine, chlorine, bromine, nitro, methyl, ethyl, methoxy and trifluoromethyl, or represents one of the radicals —S(O)$_n$—$R^9$;

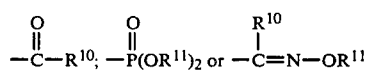

- $R^3$ independently of $R^2$ represents the same radicals as $R^2$ and additionally represents methyl, ethyl, n- and i-propyl, n-, i-, s- and t-butyl,
- $R^4$ and $R^6$ independently of one another represent cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical —S(O)$_n$—$R^{12}$,
- $R^9$ represents hydrogen, hydroxyl, fluorine, chlorine, bromine, amino, methylamino, dimethylamino, ethylamino, diethylamino, diisopropylamino, di-n-butylamino, methyl, ethyl, dichlorofluoromethyl or trifluoromethyl, and represents phenyl which is optionally mono-substituted to trisubstituted by identical or different substituents from amongst methyl, methoxy, trifluoromethyl and chlorine,
- $R^{10}$ respresents hydrogen, methyl, ethyl, n- and i-propyl, and represents phenyl which is optionally monosubstituted to trisubstituted by identical or different substituents from amongst methyl, methoxy, trifluoromethyl and chlorine, R[11] represents hydrogen, methyl, ethyl, n- and i-propyl, n-, i-, s- and t-butyl, allyl, butenyl, propargyl, benzyl, chloroethyl or bromoethyl, R[12] represents hydrogen, methyl, ethyl, n- and i-propyl, undecyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, chloropropyl or heptafluoro-n-propyl, or represents cyclopentyl, cyclohexyl or cyclopropyl which is optionally monosubstituted to tetrasubstituted by identical or different substituents from amongst fluorine, chlorine, bromine, methyl and trifluoromethyl, and represents phenyl, phenoxy, phenylthio or phenylamino, each of which is optionally monosubstituted to trisubstituted by identical or different substituents from amongst methyl, methoxy, chlorine and trifluoromethyl, and R[13] represents amino, methylamino, ethylamino, dimethylamino, diethylamino, fluorodichloromethyl, difluoromethyl, tetrafluoroethyl, trifluorochloroethyl, trifluoromethyl, methyl or ethyl.

3. The method according to claim 1, wherein the compound is 1-(2,6-dichloro-4-trifluoromethyl-phenyl)-4-nitro-5-propionylamido-pyrazole of the formula

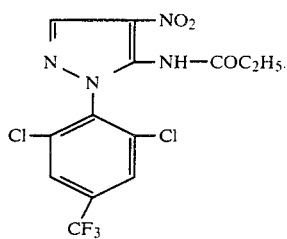

4. The method according to claim 1, wherein the compound is 1-(2-chloro-4-trifluoromethyl-phenyl)-4-nitro-5-propionylamido-pyrazole of the formula

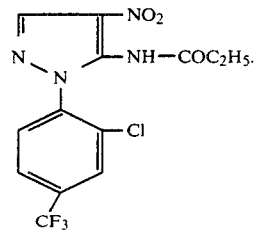

5. The method according to claim 1, wherein the compound is 1-(2-chloro-4-trifluoromethoxy-phenyl)-4-nitro-5-propionylamido-pyrazole of the formula

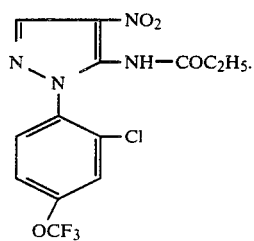

6. The method according to claim 1, wherein the compound is 5-chloroacetylamido-1-(2,6-dichloro-4-trifluoromethyl-phenyl)-pyrazole of the formula

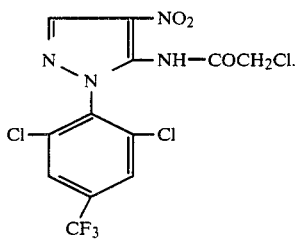

7. The method according to claim 1, wherein the compound is 5-amino-1-(2,6-dichloro-4-trifluoromethyl-phenyl)-pyrazole of the formula

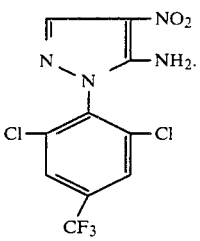

* * * * *

UNITED STATES PATENT AND TRADEMARK OFFICE
CERTIFICATE OF CORRECTION

PATENT NO. : 4,614,533　　　　　　　　　　　　　　Page 1 of 3
DATED : September 30, 1986
INVENTOR(S) : Otto Schallner, et al.

It is certified that error appears in the above-identified patent and that said Letters Patent are hereby corrected as shown below:

| | |
|---|---|
| Col. 1, line 45 | Delete "nitrose" and substitute --nitroso-- |
| Col. 4, line 34 | Delete "$R^2$" and substitute --$R^9$-- |
| Col. 7, Table 1, Col. "$R^2$", line 25 | Delete "$CH_3SCF_2$-CO" and substitute --$CH_3SCH_2$-CO-- |
| Col. 43, line 9 | Delete "3129" and substitute --3120-- |
| Col. 43, line 15 | Correct spelling of --understood-- |
| Col. 51, Table 2, column "$R^2$", line 10; | Delete "H" second instance |
| column "$R^3$", line 10, Ex. 57 | Delete "Cl" and substitute --H-- |
| column "$R^4$", line 10, Ex. 57 | Delete "H" and substitute --Cl-- |
| column "$R^5$", line 10, Ex. 57 | Delete "Cl" and substitute --H-- |
| column "$R^6$", line 10, Ex. 57 | Delete "H" and substitute --Cl-- |
| column "$R^7$", line 10, Ex. 57 | Delete "Cl" and substitute --H-- |
| column "$R^8$", line 10 Ex. 57 | Delete "102" and substitute --Cl-- |
| column "Melting point (°C.)" Ex. 57 | Insert --102-- |
| Col. 51, Table 2, Example 76, col. "$R^6$" | Delete "H" and substitute --$SCF_3$-- |
| Example 76, col. "$R^7$" | Delete "Cl" and substitute --H-- |
| Example 76, col. "$R^8$" | Delete "145-49" and substitute --Cl-- |
| Example 76, col. "Melting point (°C.)" | Insert --145-49-- |
| Col. 51, Table 2, col. "$R^5$", line 30 | Delete "$SCF_3$" |

UNITED STATES PATENT AND TRADEMARK OFFICE
CERTIFICATE OF CORRECTION

PATENT NO. : 4,614,533  Page 2 of 3
DATED : September 30, 1986
INVENTOR(S) : Otto Schallner, et al.

It is certified that error appears in the above-identified patent and that said Letters Patent is hereby corrected as shown below:

Col. 51, Table, 2,
  Example 77, col. "$R^5$"        Delete "OCFH" and substitute --H--
  Example 77, col. "$R^6$"        Insert --$OCF_3$--
  Example 77, col. "$R^7$"        Delete "Cl" and substitute --H--
  Example 77, col. "$R^8$"        Delete "206-08" and substitute
                                                                    --Cl--

Example 77, col. "Melting
  point (°C.)"                    Insert --206-08--

Col. 53, Table 2,
  Example 115, col. "$R^1$"       Delete "$CH_3CO$"
  Example 115, col. "$R^2$"       Delete "H" and substitute
                                                                  --$CH_3CO$--
  Example 115, col. "$R^3$"       Delete "Cl" and substitute --H--
  Example 115, col. "$R^4$"       Delete "H" and substitute --Cl--
  Example 115, col. "$R^5$"       Delete "$CF_3$" and substitute --H--
  Example 115, col. "$R^6$"       Delete "H" and substitute --$CF_3$--
  Example 115, col. "$R^8$"       Delete "50-52" and substitute
                                                                  --H--

Example 115, col. "Melting    Insert --50-52--
  point (°C.)"

Col. 53, Table 2,
  Example 118, col. "$R^1$"       Delete structure
  Example 118, col. "$R^2$"       Delete "H" and substitute

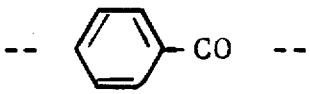

UNITED STATES PATENT AND TRADEMARK OFFICE
CERTIFICATE OF CORRECTION

PATENT NO. : 4,614,533
DATED : September 30, 1986
INVENTOR(S) : Otto Schallner, et al.

It is certified that error appears in the above-identified patent and that said Letters Patent are hereby corrected as shown below:

Col. 53, Table 2,
| | |
|---|---|
| Example 118, col. "$R^3$" | Delete "Cl" and substitute --H-- |
| Example 118, col. "$R^4$" | Delete "H" and substitute --Cl-- |
| Example 118, col. "$R^5$" | Delete "$CF_3$" and substitute --H-- |
| Example 118, col. "$R^6$" | Delete "H" and substitute --$CF_3$-- |
| Example 118, col. "$R^7$" | Delete "Cl" and substitute --H-- |
| Example 118, col. "$R^8$" | Delete "62-64" and substitute --Cl-- |
| Example 118, col. "Melting point (°C.) | Insert --62-64-- |
| Col. 57, line 39 | Before "$R^2$" delete "or" and substitute --of-- |

Signed and Sealed this

Sixth Day of January, 1987

Attest:

DONALD J. QUIGG

Attesting Officer

Commissioner of Patents and Trademarks